United States Patent
Lu et al.

(10) Patent No.: US 10,316,503 B2
(45) Date of Patent: Jun. 11, 2019

(54) AUTOMATED NURSING SYSTEM

(71) Applicants: Weidong Lu, Suzhou (CN); Qiang Song, Suzhou (CN); Shuhua Sang, Suzhou (CN); Jianjun Tan, Suzhou (CN)

(72) Inventors: Weidong Lu, Suzhou (CN); Qiang Song, Suzhou (CN); Shuhua Sang, Suzhou (CN); Jianjun Tan, Suzhou (CN)

( * ) Notice: Subject to any disclaimer, the term of this patent is extended or adjusted under 35 U.S.C. 154(b) by 1072 days.

(21) Appl. No.: 14/678,520

(22) Filed: Apr. 3, 2015

(65) Prior Publication Data

US 2015/0351984 A1   Dec. 10, 2015

Related U.S. Application Data

(60) Provisional application No. 62/075,551, filed on Nov. 5, 2014.

(30) Foreign Application Priority Data

Apr. 4, 2014 (CN) .......................... 2014 1 0135792
Apr. 4, 2014 (CN) ...................... 2014 2 0163666 U
May 6, 2014 (CN) .......................... 2014 1 0225544

(51) Int. Cl.
| | |
|---|---|
| A61G 7/00 | (2006.01) |
| A61G 7/02 | (2006.01) |
| E03F 1/00 | (2006.01) |
| A61G 9/00 | (2006.01) |
| A61G 9/02 | (2006.01) |
| A61F 5/442 | (2006.01) |
| A47K 10/48 | (2006.01) |
| A61F 5/44 | (2006.01) |
| A61F 9/02 | (2006.01) |

(52) U.S. Cl.
CPC .............. *E03F 1/006* (2013.01); *A47K 10/48* (2013.01); *A61F 5/442* (2013.01); *A61G 7/00* (2013.01); *A61G 7/02* (2013.01); *A61G 9/00* (2013.01); *A61G 9/003* (2013.01); *A61G 9/02* (2013.01)

(58) Field of Classification Search
CPC ..... A61G 7/00; A61G 7/02; F61F 5/44; A61F 9/02

See application file for complete search history.

(56) References Cited

FOREIGN PATENT DOCUMENTS

CA          2727176    * 12/2009
WO   WO 2009/151283 A2 * 12/2009

OTHER PUBLICATIONS www.evercare.co.jp.

(Continued)

*Primary Examiner* — Tatyana Zalukaeva
*Assistant Examiner* — Ilya Y Treyger
(74) *Attorney, Agent, or Firm* — K&L Gates LLP

(57) ABSTRACT

An automated nursing system for handling waste material from a patient includes a mattress including an opening; a workhead for accepting the waste material, the opening of the mattress sized to accept the workhead; a main unit in water flow and pneumatic pressure communication with the workhead; and a main processor carried by the main unit, the main processor programmed to at least partially (i) cause negative pneumatic pressure to be applied to the workhead to remove the waste material from the workhead, and (ii) cause water to be delivered to the workhead to rinse the patient.

64 Claims, 20 Drawing Sheets

(56) References Cited

OTHER PUBLICATIONS

Ever Care Home Page—Tabs 1 to 7—Japanese and translated English versions.
Tab 1—Ever Care Home—Japanese and translated English versions.
Tab 2—Merchandise Information—Japanese and translated English versions.
Tab 3—Excellence Performance of Evercare—Japanese and translated English versions.
Tab 4—Fixing Up—Japanese and translated English versions.
Tab 5—Voice—Japanese and translated English versions.
Tab 6—Q & A—Japanese and translated English versions.
Tab 7—Nursing Care Services—Japanese and translated English versions.

* cited by examiner

AUTOMATED NURSING SYSTEM

PRIORITY CLAIM

This application claims priority to and the benefit of U.S. Provisional Application Ser. No. 62/075,551, entitled, "Central Integrated Nursing System", filed Nov. 5, 2014, Chinese Patent Application No. 201410225544.8, entitled, "Central Integrated Nursing System", filed May 6, 2014, Chinese Patent Application No. 2014201636664, entitled, "A Nursing System Internal Cup", filed Apr. 4, 2014, and Chinese Patent Application No. 201410135792.3, entitled, "A Kind of Nursing Machine", filed Apr. 4, 2014, the entire contents of each of which are incorporated herein by reference and relied upon.

BACKGROUND

The present disclosure relates to the technical field of medical care devices, and in particular, to automated nursing systems.

As worldwide standard of living increases, people live longer and more people accordingly become bedridden. Bedridden patients are typically unable to transport themselves to the bathroom to excrete stool and urination, which creates hardships for the patient's family and caregivers. The help and care required increases the workload of the accompanying persons, and can cause physiological and mental suffering for the patient. To help with this problem, certain medical institutions and families of such patients use a stool and urine nursing machine to reduce the burden of the nurse or caregiver and to improve the treatment environment of the patient.

One known stool and urine (waste material) nursing machine on the market uses a sheath on the lower body of the patient to collect excrement. In both the patient's home and at the hospital, the known nursing machine has many defects. The known nursing machine requires a large space and many water lines, which causes resource waste and increases potential safety hazard. Also, the volume holding capacity for clean water and sewage for the known nursing machine are limited, causing a nurse or caregiver to (i) regularly measure and add water and (ii) drain sewage from the nursing machine to avoid shutdown of the machine, increasing the burden and workload of the nurse or caregiver.

An improved automated nursing station for handling human waster materials is needed accordingly.

SUMMARY

The system of the present disclosure addresses the deficiencies of known nursing machines by requiring less structure and floor space, being more convenient in use, and reducing the workload of the nurse or caregiver. To achieve the above advantages, the present nursing system can employ any one or more of the following technical aspects.

In a first aspect, which may be combined with any of the other aspects listed herein, an automated nursing system for handling waste material from a patient includes a mattress including an opening; a workhead for accepting the waste material, the opening of the mattress sized to accept the workhead; a main unit in water flow and pneumatic pressure communication with the workhead; and a main processor carried by the main unit, the main processor programmed to at least partially (i) cause negative pneumatic pressure to be applied to the workhead to remove the waste material from the workhead, and (ii) cause water to be delivered to the workhead to rinse the patient.

In a second aspect, which may be combined with any of the other aspects listed herein, the automated nursing system includes a hose connecting the workhead to the main unit, the hose protecting the water and pneumatic pressure communication between the workhead and the main unit.

In a third aspect, which may be combined with any of the other aspects listed herein, the workhead includes a base residing at least mostly within the opening within the mattress, and a cover extending from the base and above the mattress for covering a private area of the patient.

In a fourth aspect, which may be combined with any of the other aspects listed herein, the workhead includes a sensor for sensing the waste material, the sensor producing an output used so that the main processor can initiate (i) and (ii).

In a fifth aspect, which may be combined with the fourth aspect and any of the other aspects listed herein, the workhead includes a processor, the sensor output delivered to the workhead processor, the workhead processor in data communication with the main unit processor so that the main processor of the main unit can initiate (i) and (ii).

In a sixth aspect, which may be combined with the fifth aspect and any of the other aspects listed herein, the main unit includes a communication module and the workhead includes a communication module, and wherein the main unit processor and the workhead processor are in data communication via the main unit communication module and the workhead communication module.

In a seventh aspect, which may be combined with the sixth aspect and any of the other aspects listed herein, the communication modules are wired or wireless.

In an eighth aspect, which may be combined with any of the other aspects listed herein, the workhead includes a urine sensor and a stool sensor, the sensors producing a urine sensor output and a stool sensor output, respectively, used so that the main processor of the main unit can initiate (i) and (ii).

In a ninth aspect, which may be combined with the eighth aspect and any of the other aspects listed herein, the workhead includes a processor, the urine sensor or stool sensor output delivered to the workhead processor, the workhead processor in data communication with the main unit so that the main processor of the main unit can initiate (i) and (ii).

In a tenth aspect, which may be combined with the ninth aspect and any of the other aspects listed herein, the main unit includes a communication module and the workhead includes a communication module, and wherein the main unit processor and the workhead processor are in data communication via the main unit communication module and the workhead communication module.

In an eleventh aspect, which may be combined with the tenth aspect and any of the other aspects listed herein, the communication modules are wired or wireless.

In a twelfth aspect, which may be combined with the eighth aspect and any of the other aspects listed herein, the delivery of at least one of (i) or (ii) is different depending upon whether the urine sensor output or the stool sensor output is produced.

In a thirteenth aspect, which may be combined with any of the other aspects listed herein, the workhead includes at least one of a stool flushing nozzle, an upper private patient area flushing nozzle, a lower private patient area flushing nozzle, or a side flushing nozzle.

In a fourteenth aspect, which may be combined with the thirteenth aspect and any of the other aspects listed herein, the workhead includes a manifold for selectively delivering water to at least one of the stool flushing nozzle, upper private patient area flushing nozzle, lower private patient area flushing nozzle, or the side flushing nozzle according to a predetermined sequence.

In a fifteenth aspect, which may be combined with any of the other aspects listed herein, the workhead includes a hot air outlet positioned and arranged to dry the patient.

In a sixteenth aspect, which may be combined with any of the other aspects listed herein, the workhead includes a body type identification sensor producing an output used by the main processor or a processor of the workhead.

In a seventeenth aspect, which may be combined with the sixteenth aspect and any of the other aspects listed herein, the body type identification sensor is an optical or camera sensor.

In an eighteenth aspect, which may be combined with the sixteenth aspect and any of the other aspects listed herein, the body type identification output is used to control at least one of a level of the negative pneumatic pressure, water pressure, water volume or air temperature.

In a nineteenth aspect, which may be combined with any of the other aspects listed herein, the workhead includes an air heater and a hot air fan.

In a twentieth aspect, which may be combined with the nineteenth aspect and any of the other aspects listed herein, the main processor or a processor of the workhead controls the air heater and the hot air fan to provide hot air to dry the patient.

In a twenty-first aspect, which may be combined with any of the other aspects listed herein, the workhead defines at least one location slot for securing the workhead to a tray for receiving the workhead, the tray located within the opening of the mattress.

In a twenty-second aspect, which may be combined with any of the other aspects listed herein, the opening of the mattress receives a pad having a shaped notch for receiving the workhead.

In a twenty-third aspect, which may be combined with the twenty-second aspect and any of the other aspects listed herein, the pad is a first pad, and which includes a second at least substantially solid and same-dimensional pad placed in the opening of the mattress when the automated nursing system is not used.

In a twenty-fourth aspect, which may be combined with any of the other aspects listed herein, the main unit includes a sewage bucket, the waste material removed from the workhead into the sewage bucket.

In a twenty-fifth aspect, which may be combined with the twenty-fourth aspect and any of the other aspects listed herein, the system includes a negative pressure source in pneumatic pressure communication with the sewage bucket, the negative pressure source positioned and arranged to pull the waste material from the workhead into the sewage bucket.

In a twenty-sixth aspect, which may be combined with the twenty-fifth aspect and any of the other aspects listed herein, the negative pressure source is controlled by the main processor to perform (i).

In a twenty-seventh aspect, which may be combined with the twenty-fifth aspect and any of the other aspects listed herein, the system includes a water trap located between the sewage bucket and the negative pressure source, the water trap preventing water or water vapor in the sewage bucket from reaching the negative pressure source.

In a twenty-eighth aspect, which may be combined with the twenty-seventh aspect and any of the other aspects listed herein, the system includes a sensor positioned and arranged with respect to the water trap so as to have an output that can indicate when the water trap needs to be emptied.

In a twenty-ninth aspect, which may be combined with the twenty-eighth aspect and any of the other aspects listed herein, the main processor upon receiving the output from the water trap sensor indicating that the water trap needs to be emptied provides a corresponding user message.

In a thirtieth aspect, which may be combined with the twenty-ninth aspect and any of the other aspects listed herein, the user message is in at least one form selected from: a user readout, an audible alarm or a voice guidance output.

In a thirty-first aspect, which may be combined with the twenty-fourth aspect and any of the other aspects listed herein, the sewage bucket is configured to be removed from the main unit to remove waste material from the sewage bucket.

In a thirty-second aspect, which may be combined with the thirty-first aspect and any of the other aspects listed herein, the system includes a sensor positioned and arranged with respect to the sewage bucket so as to have an output that can indicate when the sewage bucket needs to be emptied.

In a thirty-third aspect, which may be combined with the thirty-second aspect and any of the other aspects listed herein, the main processor upon receiving the output from the sewage bucket sensor indicating that the sewage bucket needs to be emptied provides a corresponding user message.

In a thirty-fourth aspect, which may be combined with the thirty-third aspect and any of the other aspects listed herein, the user message is in at least one form selected from: a user readout, an audible alarm or a voice guidance output.

In a thirty-fifth aspect, which may be combined with the twenty-fourth aspect and any of the other aspects listed herein, the sewage bucket is in fluid communication with a drain line, the drain line for removing waste material from the sewage bucket to a house drain, toilet or sewer.

In a thirty-sixth aspect, which may be combined with the thirty-fifth aspect and any of the other aspects listed herein, the system includes a valve in the drain line, the valve selectively enabling waste material to be removed from the waste bucket.

In a thirty-seventh aspect, which may be combined with the thirty-sixth aspect and any of the other aspects listed herein, the system includes a sensor positioned and arranged with respect to the sewage bucket so as to have an output that can be used to know when to open the drain valve.

In a thirty-eighth aspect, which may be combined with the thirty-fifth aspect and any of the other aspects listed herein, the waste material is gravity fed from the sewage bucket through the drain line.

In a thirty-ninth aspect, which may be combined with any of the other aspects listed herein, the main unit includes a fresh water bucket, the water delivered to the workhead from the fresh water bucket.

In a fortieth aspect, which may be combined with the thirty-ninth aspect and any of the other aspects listed herein, the system includes a water pump in water flow communication with the fresh water bucket, the water pump positioned and arranged to pump water from the fresh water bucket to the workhead.

In a forty-first aspect, which may be combined with the fortieth aspect and any of the other aspects listed herein, the water pump is controlled by the main processor to perform (ii).

In a forty-second aspect, which may be combined with the thirty-ninth aspect and any of the other aspects listed herein, the fresh water bucket includes a removable cap for filling the bucket.

In a forty-third aspect, which may be combined with the thirty-ninth aspect and any of the other aspects listed herein, the fresh water bucket includes a spring-loaded valve for allowing water to be delivered from the bucket to the workhead.

In a forty-fourth aspect, which may be combined with the forty-third aspect and any of the other aspects listed herein, the spring-loaded valve is a check valve.

In a forty-fifth aspect, which may be combined with the thirty-ninth aspect and any of the other aspects listed herein, the fresh water bucket is in fluid communication with a fresh water line, the fresh water line for delivering fresh water from a source to the fresh water bucket.

In a forty-sixth aspect, which may be combined with the forty-fifth aspect and any of the other aspects listed herein, the system includes a valve in the fresh water line, the valve selectively enabling fresh water to be delivered to the fresh water bucket.

In a forty-seventh aspect, which may be combined with the forty-sixth aspect and any of the other aspects listed herein, the system includes a sensor positioned and arranged with respect to the fresh water bucket so as to have an output that can be used to know when to open the fresh water valve.

In a forty-eighth aspect, which may be combined with the thirty-ninth aspect and any of the other aspects listed herein, the system includes a valve in fluid communication with the fresh water bucket, the valve selectively enabling fresh water from the fresh water bucket to be circulated through at least one of a heater or an ultraviolet ("UV") disinfector.

In a forty-ninth aspect, which may be combined with the forty-eighth aspect and any of the other aspects listed herein, the system includes a temperature sensor positioned and arranged to have an output that can be used to enable fresh water to be circulated until the fresh water reaches a desired temperature.

In a fiftieth aspect, which may be combined with the forty-ninth aspect and any of the other aspects listed herein, the desired temperature is reached before (ii) can be performed.

In a fifty-first aspect, which may be combined with the forty-ninth aspect and any of the other aspects listed herein, the circulation valve is switched so that (ii) can be performed when the desired temperature has been reached.

In a fifty-second aspect, which may be combined with the forty-eighth aspect and any of the other aspects listed herein, fresh water is circulated before and/or while performing (i).

In a fifty-third aspect, which may be combined with any of the other aspects listed herein, the system includes a garment for holding the workhead against the patient.

In a fifty-fourth aspect, which may be combined with any of the other aspects listed herein, the system is configured to perform (i) and (ii) in an automatic mode or a manual mode, the manual mode enabling user selection of at least one of a stool sequence, a urine sequence, a flush sequence, a clean sequence, or a dry sequence.

In a fifty-fifth aspect, which may be combined with the fifty-fourth aspect and any of the other aspects listed herein, the automatic mode is a default mode.

In a fifty-sixth aspect, which may be combined with the fifty-fourth aspect and any of the other aspects listed herein, at least one of the automatic mode or the manual mode is selected via a remote controller.

In a fifty-seventh aspect, which may be combined with any of the other aspects listed herein, at least one operating parameter of the system is user-selectable.

In a fifty-eighth aspect, which may be combined with the fifty-seventh aspect and any of the other aspects listed herein, the at least one operating parameter includes water temperature, water pressure and air temperature.

In a fifty-ninth aspect, which may be combined with any of the other aspects listed herein, the main unit includes a music player configured to play music supplied by the patient or user.

In a sixtieth aspect, which may be combined with any of the other aspects listed herein, the workhead is a first workhead, and which includes at least one second workhead in water flow and pneumatic pressure communication with the main unit.

In a sixty-first aspect, which may be combined with the sixtieth aspect and any of the other aspects listed herein, the system includes a water flow manifold that allows water to be selectively delivered to the first workhead or to one of the at least one second workheads to perform (ii).

In a sixty-second aspect, which may be combined with the sixty-first aspect and any of the other aspects listed herein, the manifold includes a plurality of solenoid valves controlled by the main processor.

In a sixty-third aspect, which may be combined with the sixtieth aspect and any of the other aspects listed herein, the system includes a negative pressure manifold that allows negative pressure to be selectively applied to the first workhead or one of the at least one second workheads to perform (i).

In a sixty-fourth aspect, which may be combined with the sixty-third aspect and any of the other aspects listed herein, the manifold includes a plurality of solenoid valves controlled by the main processor.

In a sixty-fifth aspect, which may be combined with any of the other aspects listed herein, a central integrated nursing system is provided and includes a main unit and a plurality of workheads, wherein a sewage suction device, a fresh water subassembly, a main unit processor and a main unit communication module are arranged on the main unit. A drainage line (tube, pipe or hose) connected with a sewer can be arranged on the sewage suction device. An intake line (tube, pipe or hose) connected with a tap water source can be arranged on the water supply device. Main unit processor can be connected respectively with the sewage suction device, the fresh water subassembly and the main unit communication module via electrical circuits. The plurality of workheads can be connected respectively with the sewage suction device and the fresh water subassembly on the main unit via water lines (tubes, pipes or hoses). Further, the plurality of workheads can be connected respectively with the main unit communication module on the main unit via data transmission interfaces, e.g., Ethernet or wireless interfaces.

In a sixty-sixth aspect, which may be combined with the sixty-fifth aspect and any of the other aspects listed herein, the sewage suction device includes a sewage bucket and a negative pressure source. The sewage bucket can be connected with the negative pressure source via an air line (tube, pipe or hose). Moreover, the drainage line (tube, pipe or hose) connected with the sewer can be arranged on the sewage bucket. A sewage selector can be arranged on the sewage bucket. The plurality of workheads can be connected respectively with the sewage selector via a water line, while the main unit processor can be connected with the sewage selector via an electrical circuit.

In a sixty-seventh aspect, which may be combined with the sixty-fifth aspect and any of the other aspects listed herein, a water trap is connected to and arranged on an air line located between the sewage bucket and the negative pressure source. The water trap includes a pedestal and an impounding cup. The upper end of the pedestal can be provided with an intake adapter and an exhaust adapter. An impounding cup is arranged at the intake adapter corresponding to the lower end of the pedestal. A first sensor for detecting the liquid level of the impounding cup can be arranged on the impounding cup. The first sensor can be connected with the main unit processor via an electrical circuit, while the lower end of the impounding cup can be provided with a drain cock. The first sensor can be a capacitive, inductive or optical sensor. An impermeable ball matched with the exhaust adapter can be arranged in the pedestal. The upper end of the exhaust adapter can be provided with a filtering joint. The intake adapter can be connected with the sewage bucket via a water line (tube, pipe or hose), while the exhaust adapter can be connected with the negative pressure source via an air line.

In a sixty-eighth aspect, which may be combined with the sixty-fifth aspect and any of the other aspects listed herein, a drainage on-off valve is arranged on a drainage line, while a second sensor for detecting a liquid level of the sewage bucket can be arranged on the sewage bucket. A drainage on-off valve and the second sensor can be connected respectively with the main unit processor via an electrical circuit. The second sensor can also be a capacitive, inductive or optical sensor.

In a sixty-ninth aspect, which may be combined with the sixty-fifth aspect and any of the other aspects listed herein, the fresh water subassembly includes a fresh water bucket, a second shunt valve, a positive temperature efficient ("PTC") heater, a smaller water pump, a larger water pump and an ultraviolet ("UV") disinfector. The intake line (tube, pipe or hose) connected with the tap water source can be arranged on a fresh water bucket. The fresh water bucket, the second shunt valve, the smaller water pump, the PTC heating device and the UV disinfector can be connected fluidically via a water line in sequence. Also, the UV disinfector can be connected with the fresh water bucket via a water line (tube, pipe or hose). The larger water pump can be connected with the second shunt valve via a water line. The second shunt valve, the PTC heating device, the smaller water pump, the larger water pump and the UV disinfector can be connected respectively with the main unit processor via electric circuits, while the plurality of workheads can be connected with the larger water pump via water lines (tubes, pipes or hoses).

In a seventieth aspect, which may be combined with the sixty-fifth aspect and any of the other aspects listed herein, a clean water selector is arranged on the larger water pump. The plurality of workheads are connected respectively with the clean water selector via water lines, while the clean water selector is connected with the main unit processor via an electrical circuit.

In a seventy-first aspect, which may be combined with the sixty-fifth aspect and any of the other aspects listed herein, a waste container, a drying device, a first shunt valve, an extension processor and a extension communication module can be arranged on the workhead. The waste containers on the plurality of workheads can be connected respectively with the sewage suction device on the main unit via sewage lines (tubes, pipes or hoses). The inner wall of the waste container can be provided with a plurality of cleaning nozzles. The plurality of cleaning nozzles can be connected respectively with the first shunt valve. The first shunt valve on the plurality of workheads can be connected respectively with the fresh water subassembly on the main unit via a water line (tube, pipe or hose). The drying device can be connected with and arranged on a rear side wall of the waste container, for example, just opposite to the opening of the workhead. An extension or local processor can be connected respectively with the first shunt valve via an extension or local communication module and via electrical circuits. The extension or local communication modules on the plurality of workheads can be connected respectively with the main unit communication module on the main unit, for example, via data transmission, e.g., Ethernet or wireless transmission.

In a seventy-second aspect, which may be combined with the sixty-fifth aspect and any of the other aspects listed herein, a stool sensor and a urine sensor are arranged on the inner wall of the waste container. The stool sensor and the urine sensor can be connected respectively with the extension processor via electrical circuits. The stool sensor can be a pressure sensor or strain gauge, while the urine sensor can be a wetness sensor, such as a conductivity sensor.

In a seventy-third aspect, which may be combined with the sixty-fifth aspect and any of the other aspects listed herein, the plurality of cleaning nozzles include a spraying nozzle spraying to the lower body of a patient, a flushing nozzle spraying to the inner wall of the waste container and an excrement flushing nozzle for spraying excrement. The spraying nozzle, the flushing nozzle and the excrement flushing nozzle can be connected respectively with the first shunt valve via water lines. The spraying nozzle can be arranged on the rear side wall of the waste container, for example, just opposite to the opening of the workhead. The flushing nozzle can be arranged at the edges at the two sides of the opening of the waste container, while the flushing nozzle may translate back and forth along the edge of the opening of the waste container, and while the excrement flushing nozzle is arranged at the front edge of the opening of the waste container.

In a seventy-fourth aspect, which may be combined with the sixty-fifth aspect and any of the other aspects listed herein, the first shunt valves on the plurality of workheads are connected respectively with a clean water selector on the main unit via water lines (tubes, pipes or hoses). A sewage output of the waste container can be connected with the sewage selector via a water line.

In a seventy-fifth aspect, any of the structures, features, operations and alternatives thereof illustrated and described in connection with FIGS. 1 to 26 may be combined with any of the other aspects listed herein.

The present disclosure has the advantageous effects that through the provision of one main unit and one or more of the foregoing workheads, device configuration and operation costs of a hospital or a patient care area are reduced. A system shutdown caused by a water shortage and/or a full loading of a sewage bucket are avoided due to the connection, in one embodiment, of the main unit with the house or hospital sewer and the tap water sources in the hospital or care area. In addition, regular cleaning and maintenance by the nurse or caregiver is reduced or eliminated.

Additional features and advantages of the present invention are described in, and will be apparent from, the following Detailed Description of the Invention and the figures.

DETAILED DESCRIPTION

System Overview

Figure 1:
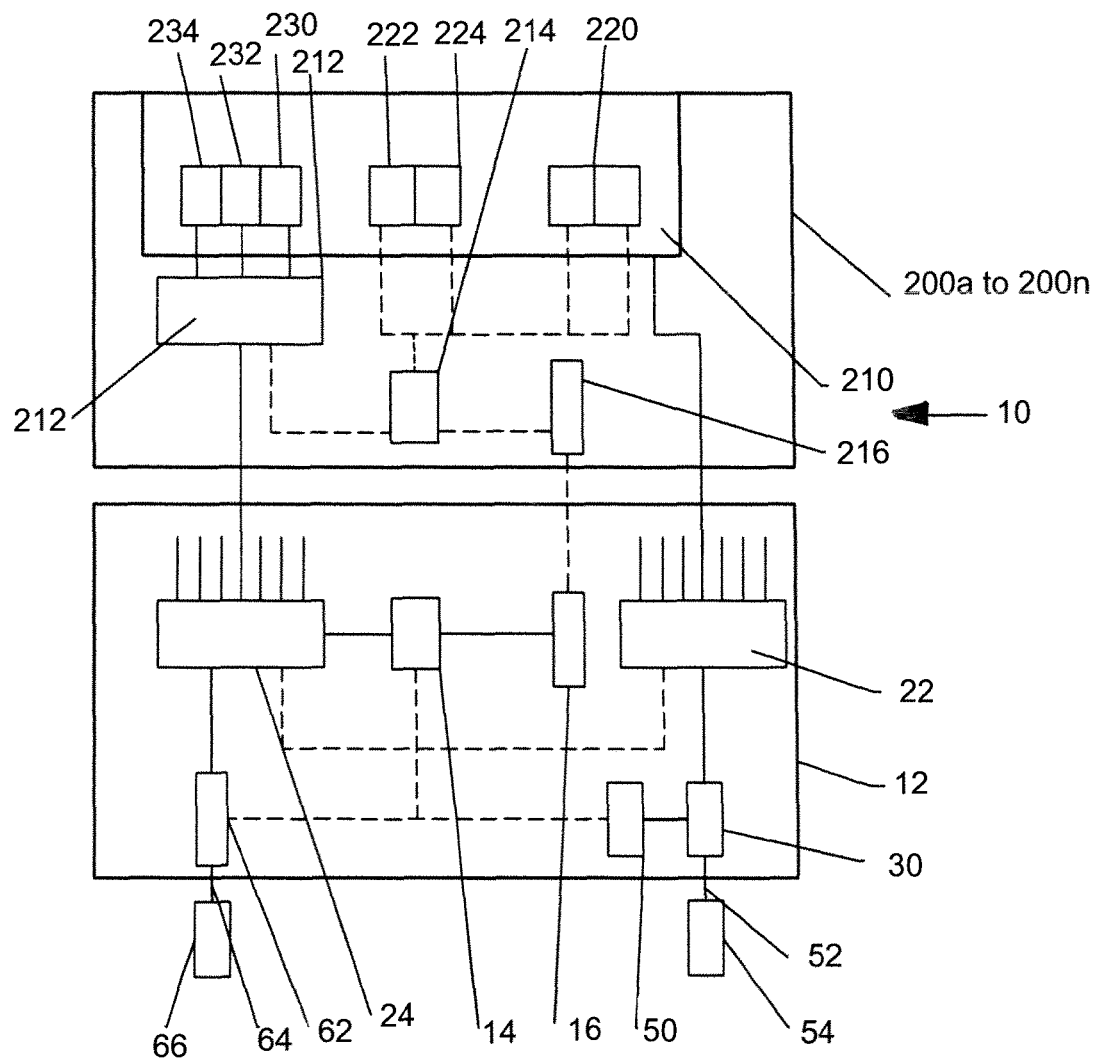
FIG. 1 is a schematic diagram of a one embodiment of a connecting relationship between different components of the nursing system of the present disclosure.

Referring now to the drawings and in particular to FIG. 1, a schematic drawing illustrating an overview of an automated nursing system 10 is illustrated. In FIG. 1, solid lines connecting the elements drawn symbolically as boxes are water and/or pneumatic lines, while dashed lines connecting the elements are electrical and/or signal lines. System 10 includes a main unit 12 that communicates fluidically, pneumatically and electrically (including data signals) with one or more workhead 200a, 200b, 200c . . . 200n (referred to collectively as workheads 200 or singly and generally as workhead 200, only one workhead illustrated in FIG. 1). Main machine 12 includes among other items, a main central processing unit ("CPU") 14, and a main unit communication module 16, such as an Ethernet module or a wireless communication module, in data communication with main CPU or processor 14. As illustrated below, for example at FIGS. 5 and 6, main CPU 14 also operates with a user interface 18 and a data input port 20, such as a USB port.

System 10 can be provided in different fundamental variations. In one fundamental variation, main unit 12 is either built for use with a single workhead 200 or multiple workheads 200. For example, single workhead version of system 10 can be provided for use in a home with a single patient. Here, main unit 12 has only one hose connection for a single hose to connect between main unit 12 and single workhead 200. In a hospital environment, however, a multiple workhead version of system 10 can be provided, so that a single main unit 12 can operate multiple workheads 12 for multiple patients. Here, main unit 12 has plural hose connections for plural hoses to connect between main unit 12 and multiple workheads 200.

In the system 10 version operating with multiple workheads 200, there needs to be a way for main unit 12 to select between workhead 200c, versus workhead 200a, versus workhead 200b, and so on. In one solution, system 10 provides two separate valve manifolds, namely, a pneumatic manifold 22 and a water manifold 24. Each of pneumatic manifold 22 and water manifold 24 in an embodiment includes a plurality of electrically actuated solenoid valves (not illustrated), for example, a separate solenoid valve for each of the seven line segments (for seven workheads) extending from pneumatic manifold 22 and water manifold 24 in FIG. 1. Each solenoid valve could for example be a normally closed valve that opens when powered via main processor 14. When opened, the solenoid valves allow for water and/or pneumatic communication between main unit 12 and one of the workheads 200.

In particular, the solenoid valves for pneumatic manifold 22 of main unit 12 allow for selective waste material and pneumatic communication between a desired one of the, e.g., seven, workheads 200a to 200g and a sewage bucket 30, which is in pneumatic communication with a negative pressure or vacuum source 50. Vacuum source 50, as illustrated in FIG. 1 is in electrical communication with main CPU 14, such that main CPU 14 can selectively actuate vacuum source 50 and one of the solenoid valves of manifold 22 based on a computer program running on CPU 14 to apply a vacuum to a desired workhead 200*a* to 200*g*, to in turn pull waster material (stool or urine) from the desired workhead 200, through manifold 22, into sewage bucket 30.

The solenoid valves for water manifold 24 of main unit 12 allow for selective water communication between a desired one of the, e.g., seven, workheads 200*a* to 200*g* and a fresh water bucket 62 illustrated in FIG. 1. Fresh water bucket 62 is part of an overall fresh water subassembly 60 described in detail below. Fresh water bucket 62 receives fresh water, which is heated and disinfected as discussed in detail below, for rinsing the patient and/or workhead 200. Water manifold 24 is likewise in electrical communication with main CPU 14, such that CPU 14 can selectively actuate a desired one of the manifolds of water manifold 24 and a water pump of fresh water subassembly 60 based on a computer program running on CPU 14 to supply heated, disinfected water from fresh water bucket 62, through manifold 24, to a desired one of the, e.g., seven, workheads 200*a* to 200*g*.

In the system 10 version operating with only a single workhead 200, pneumatic and/or water manifolds 22 and 24 are not needed. Here instead, CPU 14 selectively actuates vacuum source 50 based on a computer program running on CPU 14 to apply a vacuum to the single workhead 200 to in turn pull waster material (stool or urine) from the workhead 200 into sewage bucket 30. CPU 14 also selectively actuates a water pump of fresh water subassembly 60 based on a computer program running on CPU 14 to supply heated, disinfected water from fresh water bucket 62 to the single workhead 200.

In a second fundamental variation, main unit 12 is either built as a standalone unit or as a unit intended for connection to a house drain, toilet or sewer and for connection to a house water tap. There may be use scenarios, e.g., apartments or logistically difficult settings, where connection between main unit 12 and a house drain, toilet or sewer and/or water tap is difficult. In such cases, a version of automated nursing system 10 with a removable sewage bucket 30 and a removable fresh water bucket 62 is provided. Removable sewage bucket 30 is removed and emptied when it is full, e.g., when sensed by a sensor, and then returned to main unit 12. Removable fresh water bucket 62 is removed and filled with fresh water when it is empty or near empty, e.g., when sensed by a sensor, and then returned to main unit 12.

In other use scenarios, e.g., hospitals and households with proper logistics, main unit 12 can be connected (i) to a house drain, toilet or sewer to remove waste products from sewage bucket 30 and (ii) to a house water tap to fill fresh water bucket 62. Here, sewage bucket 30 communicates fluidly with a drain line 52 provided by main unit 12, which allows waste materials to be gravity fed, for example, to a house drain, toilet or sewer 54, as illustrated in FIG. 1. Likewise, water bucket 62 communicates fluidly with a fresh water line 64 provided by main unit 12, which allows fresh water to be delivered from a source or tap 66 to fresh water bucket 62. As discussed in detail below, drain line 52 can be provided with a drain line valve, which main processor 14 opens in one embodiment upon receiving a signal that sewage bucket 30 is full or nearly full. Likewise, fresh water line 64 can be provided with a fresh water line valve, which main processor 14 opens in one embodiment upon receiving a signal that fresh water bucket 62 is empty or nearly empty.

FIG. 1 illustrates two water/pneumatic lines leading from main unit 12 to workhead 200. Both of those lines can be placed within a single hose leading from the main unit to the workhead, along with one or more electrical/signal line (shown as dashed in FIG. 1). However, since the vacuum from vacuum source 50 is supplied at a different time than is the fresh water from fresh water bucket 62 of fresh water subassembly 60, it is contemplated that two water/pneumatic lines can be merged into a single line, which is shared for both purposes. Here, main processor 14 can electrically control a three-way valve (not illustrated in FIG. 1) to select either waste material/pneumatic flow via vacuum source 50 for waster material removal from workhead 200, or fresh water flow from fresh water bucket 62 of fresh water subassembly 60 to workhead 200 for flushing and cleaning A primary component of each workhead 200*a*, 200*b*, 200*c* . . . 200*n* of system 12 as illustrated by the darkened box in FIG. 1 is waste container 210. Waste container 210 receives the sewage line extending from pneumatic manifold 22 (optional as explained above) of main unit 12. Waste container 210 in the illustrated embodiment of FIG. 1 also receives three fresh water lines extending from a fresh water manifold 212. Fresh water manifold 212 of workhead 200, just like manifolds 22 and 24 of main unit 12, can include electrically actuated solenoid valves, one or more of which can be opened selectively to allow fresh water to be delivered to different one or more places within waste container 210 of workhead 200. In the embodiment illustrated in FIG. 1, each workhead 200 includes its own workhead processor or CPU 214. Workhead processor 214 controls local functions particular to workhead 200, such as the selection of which of the solenoid valves within fresh water manifold 212 to open. It should be appreciated however that workhead processor 214 can be eliminated, such that main processor 14 of main unit 12 also receives inputs from and sends outputs to each workhead 200. When main processor 14 controls both main unit 12 and workheads 200, more electrical/data wires have to be run between main unit 12 and each workhead 200. Workhead processor 214 allows the hose wires to be reduced to data transfer wires and signal wires.

In the embodiment illustrated in FIG. 1, main processor 14 is in data communication with main unit communication module 16, while workhead processor 214 is in data communication with a workhead communication module 216. Communication modules 16 and 216 can each be a wired Ethernet module or a wireless communication module, such as a Wi-Fi, Bluetooth or ZigBee module. Communication modules 16 and 216 enable processors 14 and 214 to talk and share data with each other. It should be appreciated however that while the remainder of FIG. 1 is explained using communication modules 16 and 216 and processors 14 and 214, workhead communication module 216 and processor 214 can be eliminated, such that only main processor 14 and communication module 16 are provided and used (communication module 16 would still be used with a remote controller discussed below).

FIG. 1 also illustrates that waste container 210 of each workhead 200 operates with a heating unit 220 that blows warm air onto the patient to dry the patient. FIG. 1 shows two dashed or electrical lines running from workhead processor 214 to heating unit 220. The two lines are provided because heating unit 220 includes two electrical components, namely, an air heater and a fan, which are powered and depowered simultaneously in one embodiment. Heating unit or drying device is activated via workhead processor 214 or main unit processor 14 after a fresh water flush of waste container 210 and the patient to dry the container and the patient.

FIG. 1 further illustrates that waste container 210 positions and arranges a stool sensor 222 and a urine sensor 224

(e.g., at the bottom of the container) to sense stool and urine, respectively, within the container. Stool sensor 222 can be a weight or pressure sensor, such as a load cell or strain gauge. Urine sensor 224 can be a liquid sensor, such as a wetness sensor or conductivity sensor. Sensors 222 and 224 are connected electrically to, and are in data signal communication with, workhead processor 214 of each workhead 200a, 200b, 200c . . . 200n (or main processor 14), and in in one embodiment begin the automated cleaning process. When human waste is detected via sensors 222 and 224, workhead processor 214 and main processor 14 communicate via communication modules 216 and 16 in one embodiment to cause vacuum source 50 to pull the waste from waste container 210 of workhead 220 into sewage bucket 30 of main unit 12, after which main processor 14 causes fresh water subassembly 60 to deliver heated and disinfected fresh water from fresh water bucket 62 into waste container 210 to clean and rinse the container and the patient of any waste residue. Upon rinse completion, workhead processor 214 (or main processor 12) powers heating unit 220 to dry container 210 and the patient.

For the above-described rinsing, FIG. 1 illustrates that waste container 210 is provided with upper and lower private part nozzles or sprayers 230, side flushing nozzles or sprayers 232, and waste material flushing nozzles or sprayers 234 to clean and rinse the patient and waste container 210 of any waste residue. The nozzles are placed at different locations within waste container 210 and are operated according to a spraying program run on local workhead processor 214 or on main processor 14. Local workhead processor 214 or main processor 12 is in electrical communication with fresh water manifold 212, which as discussed above can include an electrically actuated solenoid valve for each of nozzles 230, 232 and 234. In FIG. 1, a separate hot/disinfected water line is illustrated running from fresh water manifold 212 to each of nozzles 230, 232 and 234. In this configuration, workhead processor 214 or main processor 14 according to a computer program can allow hot, disinfected water to flow to one or more of nozzles 230, 232 and 234 at the same time and/or at separate times in a programmed sequence.

Figure 2:
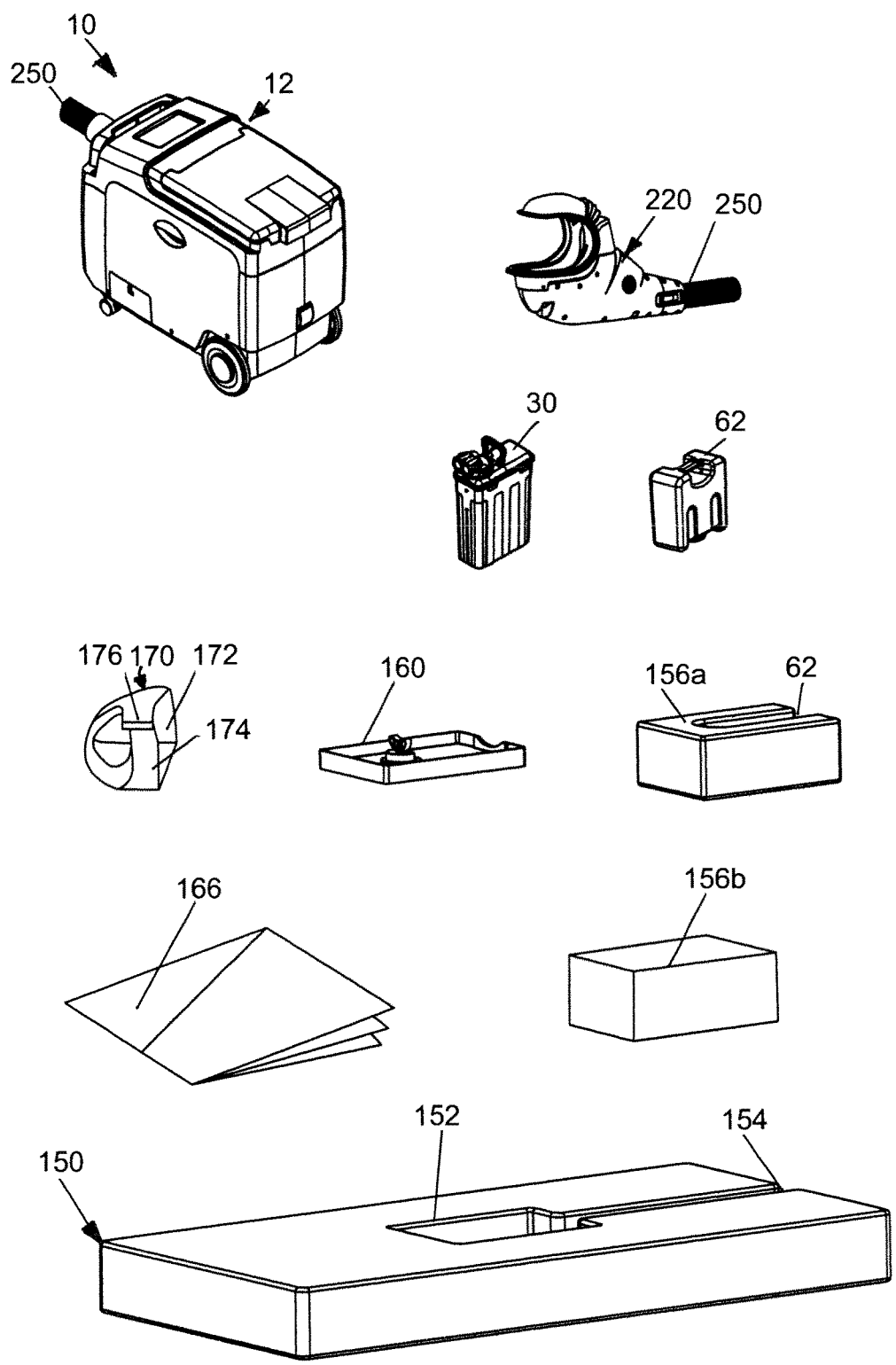
FIG. 2 is a perspective view of one embodiment of various components of the nursing system of the present disclosure.

Referring now to FIG. 2, the main components of system 10 are illustrated. Many of the components have been discussed above, including main unit 12 having sewage bucket 30, water bucket 62, and workhead 220. A hose 250 extends between main unit 12 and workhead 220 and carries waste material/pneumatic, fresh water and electrical/data lines.

System 10 further includes a mattress 150. Mattress 150 as illustrated defines an opening 152 that accepts workhead 220. Opening 152 communicates with a slot 154 extending through an end of mattress 150, so that hose 250 has a route to extend easily from mattress 150 to main unit 12. Opening 152 is sized to removably accept a tray 160 that accepts and removably holds workhead 220. Opening 152 is also sized to removably accept a pad 156a having a notch 158 shaped to snugly accept workhead 220. When system 10 is not in use, pad 156a can be removed and replaced with a substantially same sized solid pad 156b, so that opening 152 is filled. System 10 further includes a sheet 166.

A garment 170 is provided, which is worn by a patient to couple workhead 220 to the patient. Garment 170 includes a hole 172 that extends around workhead 220 and the patient. Garment includes flaps 174 and 176, the ends of which releaseably attach to each other, e.g., via a hook and loop type of connection.

Figure 3:
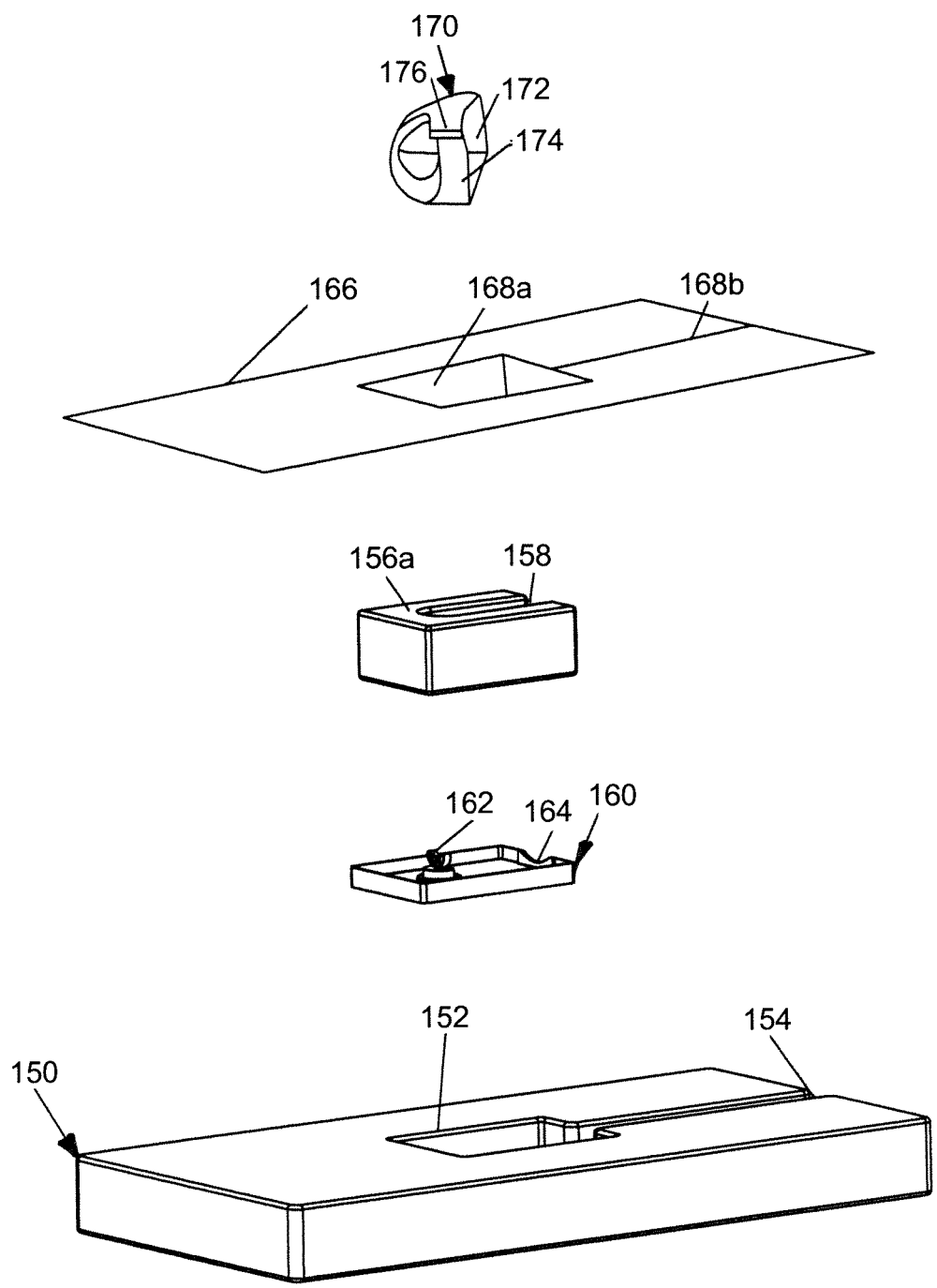
FIG. 3 is a perspective view of one embodiment of various components of a mattress assembly of the nursing system of the present disclosure.

FIG. 3 illustrates the order in which the mattress arrangement is installed. Mattress 150 is placed on a hospital or home bed (not illustrated). Tray 160 is then placed into opening 152 of mattress 150. Pad 156a with shaped notch 158 is then placed into opening 152 of mattress 150, on top of tray 160. The mattress 150 is then outfitted with a sheet 166 having a hole 168a and slit 168b positioned to match opening 152 and slot 154 of mattress 150, respectively. Garment 170 with hole 172 facing the slotted end of mattress 154 is then inserted into shaped notch 158 of pad 156a. Workhead 220 is then laid onto garment 170 and fitted into shaped notch 158 of pad 156a, coming to rest on tray 160. Workhead 220 includes two location slots. One of the slots of workhead 220 rests upon a spring-loaded, arced pedestal 162 of tray 160, while another slot rests upon a cutout 164 provided in the mating end wall of tray 160. The connection of the workhead slots to tray 160 prevents workhead from sliding back and forth along the long axis of mattress 150.

Figure 4:
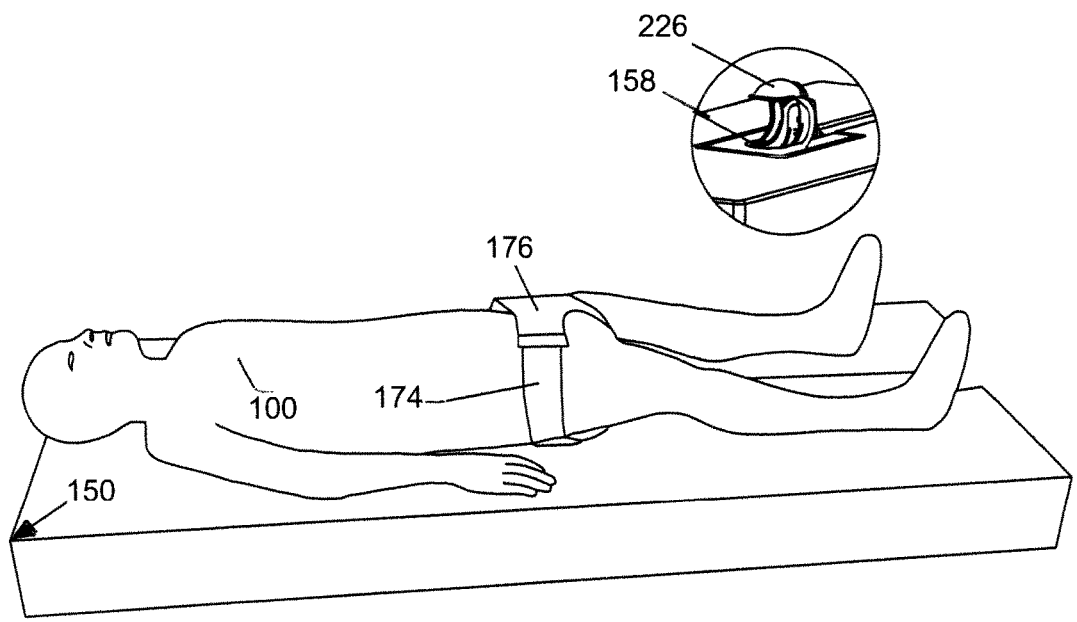
FIG. 4 is a perspective view of one embodiment of how a patient interacts with the nursing system of the present disclosure.

FIG. 4 illustrates patient 100 lying on mattress 150. The zoomed-in bubble of FIG. 4 illustrates that a silicone cover 226 of workhead 220 extends up from the top of mattress 150 through the shaped notch 158 of pad 156a. Patient 100 lies on mattress 150 so that the patient's private areas become covered by silicone cover 226 of workhead 220. Patient 100 or a caregiver then pulls flaps 174 and 176 of garment 170 up over the top of silicone cover 226 and attaches the ends of flaps 174 and 176 together to secure silicone cover 226 to patient 100.

Main Unit

Referring now to FIGS. 5 to 14, main unit 12 is illustrated and described in more detail. FIGS. 5, 6, 7, 8 and 9 illustrate a version of main unit 12 in which (i) main unit 12 operates with only a single workhead 200 and (ii) main unit 12 is self-contained such that it is not connected to a house drain, toilet or sewer 54 or to a fresh water tap 66 (illustrated in FIG. 1). It should be appreciated however that, except where noted, each of the features, structure, functionality and alternatives described in connection with FIGS. 5, 6, 7, 8 and 9 is also included in the version of main unit 12, in which (i) main unit 12 operates with multiple workheads 200 and (ii) main unit 12 is connected to a house drain, toilet or sewer 54 (illustrated in FIG. 1) and a fresh water tap 66 (illustrated in FIG. 1).

Figure 5:
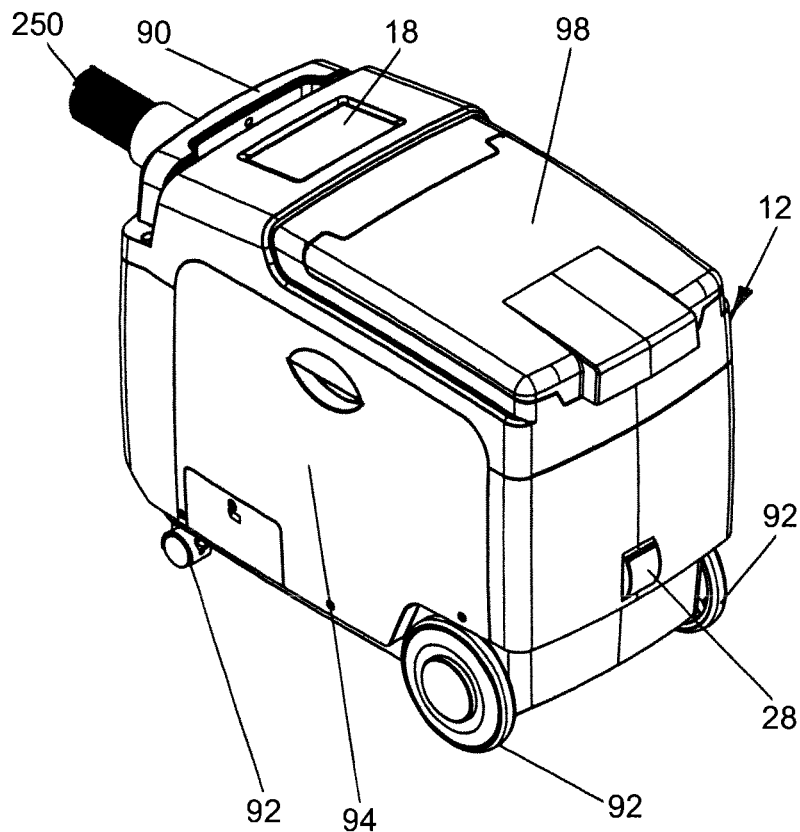
FIG. 5 is a top-rear perspective view of one embodiment of a main unit of the nursing system of the present disclosure.
Figure 6:
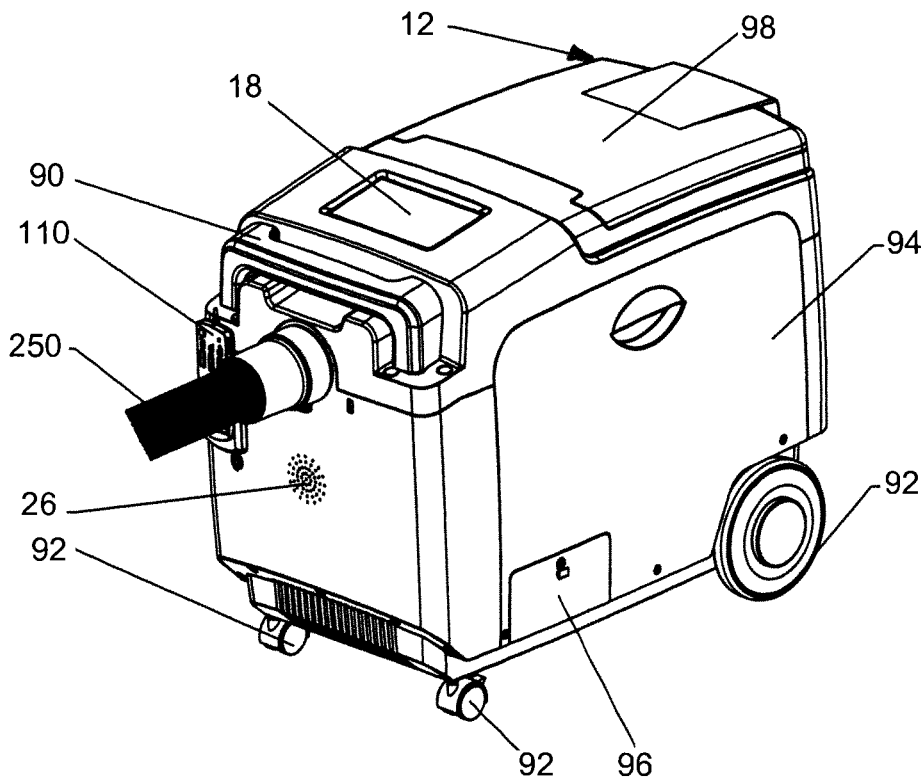
FIG. 6 is a top-front perspective view of one embodiment of a main unit of the nursing system of the present disclosure.
Figure 9:
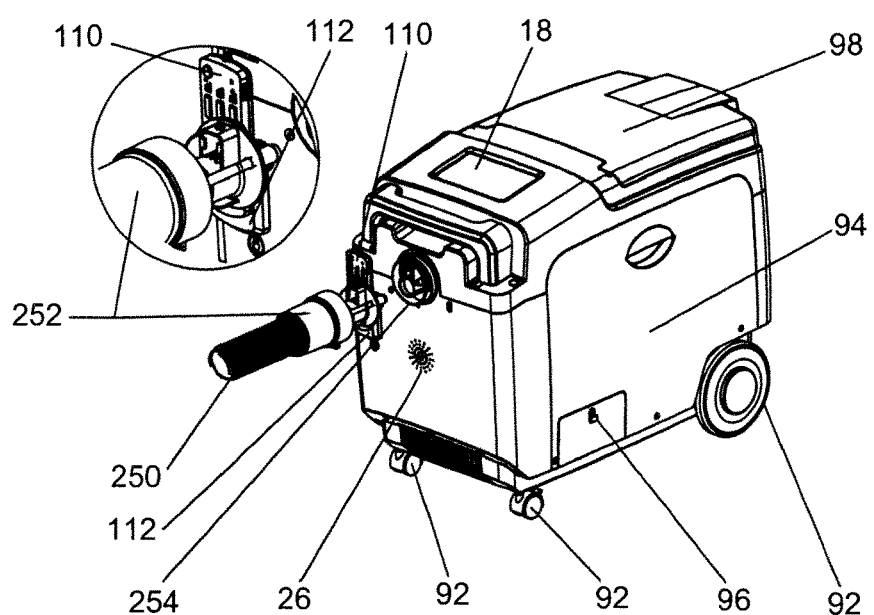
FIG. 9 is a top-front perspective view of one embodiment of a main unit of the nursing system of the present disclosure illustrating a hose connection.

FIGS. 5 and 6 illustrate that main unit 12 includes user interface 18 and a data input port 20. User interface 18 can include a light emitting display ("LED"), liquid crystal display ("LCD") or other type of display as desired. User interface 18 can include a touch screen overlay used with the display and/or provide off-screen electromechanical buttons, such as membrane switches. FIGS. 6 and 9 illustrate that main unit 12 receives user input alternatively or additionally from a remote controller 110. Remote controller 110 is in one embodiment connected to main unit 12 via a cord for wired connection with, e.g., Ethernet, with main unit communication module 16. Remote controller 110 in another embodiment interfaces with main processor 14 via a wireless main unit communication module 16 discussed above in connection with FIG. 1. Main unit 12 as illustrated in FIGS. 6 and 9 can provide a slot 112 to receive remote controller 110.

FIG. 9 also shows an exploded view for connecting connector 252 of hose 250 to connector 254 of main machine 10. In the illustrated embodiment, the user simply presses hose connector 252 onto main machine connector 254. To do so, the user aligns the different water, pneumatic and/or electrical connections within connectors 252 and 254 and then presses the connectors together, making releaseably fluid tight and air tight connections where needed.

Data input port 20 can be a universal serial bus ("USB") port, which accepts peripheral device inputs, such as the patient's music playing device, e.g., an MP3 player, smart phone or iPod. FIGS. 6 and 9 illustrate that main unit 12 includes a speaker 26 operable with main processor 14 for outputting music, audible alarms, voice guidance instructions and the like. Any alarms or alerts associated with the operation of system 10 can alternatively or additionally be displayed on the display device of user interface 18. User interface 18 and/or voice guidance instructions via speaker 26 can be provided to walk the patient or user through any setup procedure (e.g., patient connection to workhead 200), operational function (e.g., bucket emptying or filling), alarm troubleshooting (e.g., water trap full, sewage bucket full, fresh water bucket low), and the like. Main unit 12 provides an on/off switch 28 for selectively powering the unit.

Figure 7:
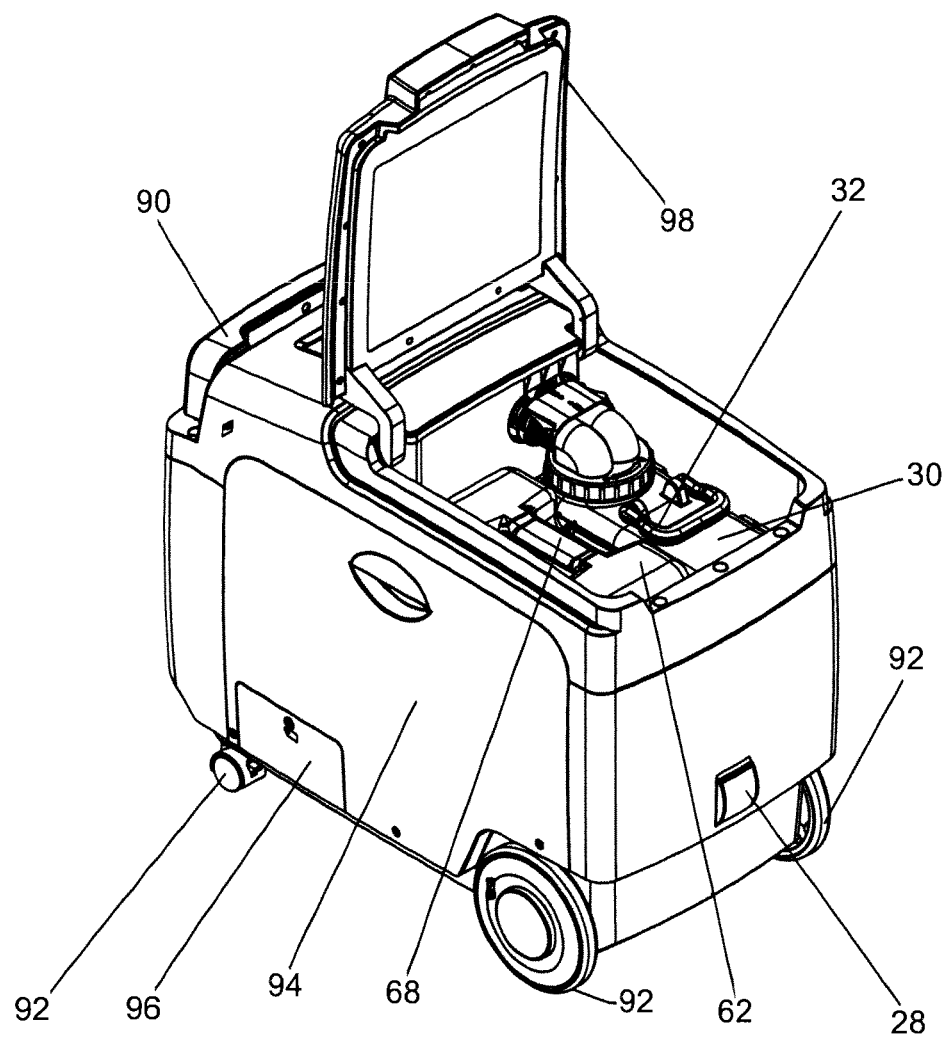
FIG. 7 is a top-rear perspective view of one embodiment of a main unit of the nursing system of the present disclosure having an open access panel.
Figure 8:
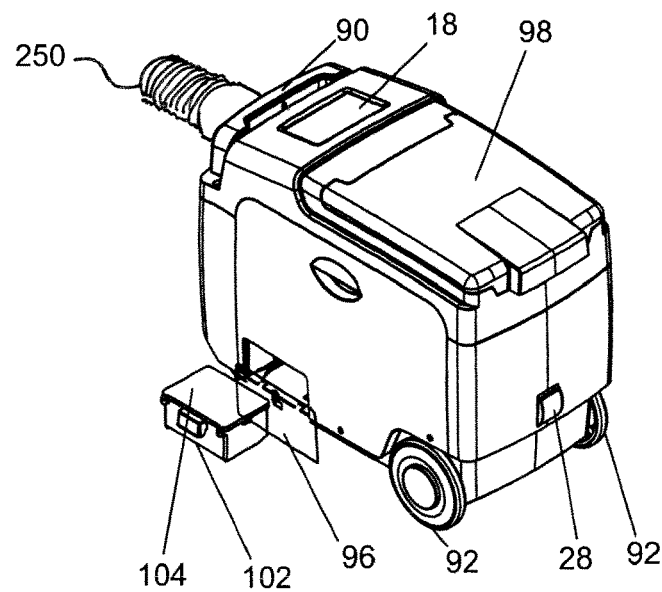
FIG. 8 is a top-rear perspective view of one embodiment of a main unit of the nursing system of the present disclosure having a removed deodorization component.

FIGS. 5, 6, 7, 8 and 9 illustrate that main unit 12 includes a pop-up and fold-down handle 90 and wheels 92 for readily transporting the main unit. Each side of main unit 12 includes a removable access panel 94 for accessing components within main unit 12. In an embodiment, the user removes screws to remove side access panels 94. A separate access panel 96 is provided to enclose a deodorization component 102. FIG. 8 illustrates access panel 96 opened and deodorization component 102 removed. The user opens access panel 96 in one embodiment by pressing the top of the access panel and then releasing pressure, allowing the hinged access panel 96 to swing open. Deodorization component 102 can then be removed from main unit to replace a deodorizer within deodorization component 102 if necessary. In an embodiment, a top 104 of deodorization component 102 is removed by unscrewing fasteners holding top 104 to the base of deodorization component 102.

FIG. 7 illustrates that an access panel 98 provided on the top of main unit 12 can be swung open to expose sewage bucket 30 and fresh water bucket 62. As discussed above, the version of main unit 12 illustrated in FIGS. 5, 6, 7, 8 and 9 requires a user to remove sewage bucket 30 to empty the bucket and to remove fresh water bucket 62 to fill the bucket with fresh water. FIG. 7 illustrates that sewage bucket 30 includes a handle 32, while fresh water bucket 62 includes a handle 68 for lifting the buckets out of main unit 12 when access panel 98 is opened.

Figure 10A:
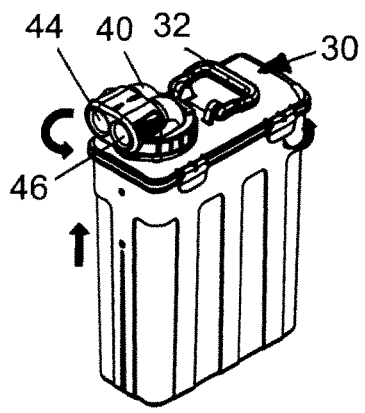
FIGS. 10A to 10C are perspective and front views of one embodiment of a sewage bucket of the nursing system of the present disclosure.
Figure 10B:
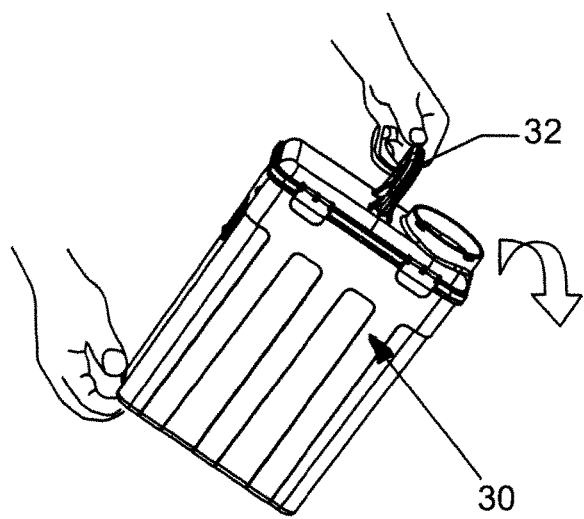
Figure 10C:
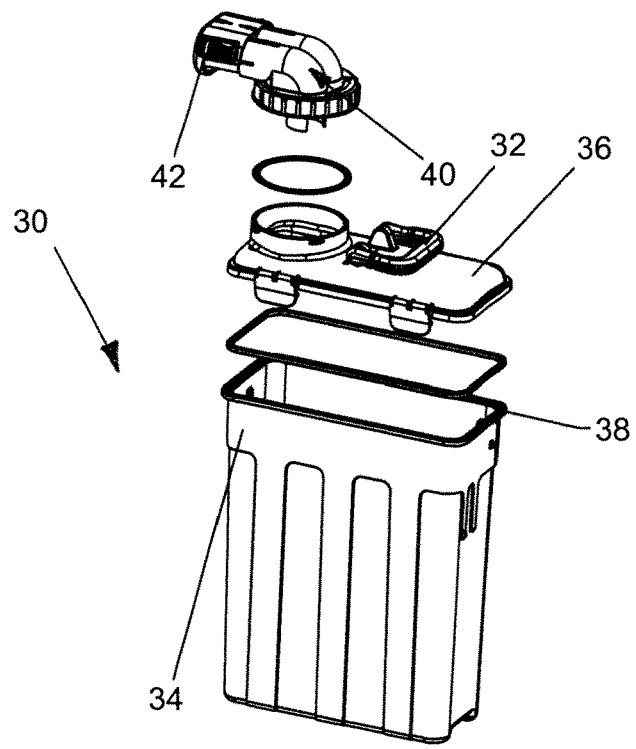

FIGS. 10A to 10C illustrate sewage bucket 30 in more detail. Sewage bucket 30 can be taken apart as illustrated in FIG. 10C to expose a base container 34, a lid 36, and an O-ring seal provided to seal lid 36 when clamped onto base container 34 via hinged pinching clips. Lid 36 includes handle 32 and a cap 40. FIG. 10B illustrates that cap 40 can be removed from lid 36, such that sewage can be poured from base container 34. Base container 34 can then be rinsed with toilet cleaner or other agent for cleaning and disinfecting.

FIGS. 7 and 10C illustrate that cap 40 includes a sliding device 42 that removably locks and seals the openings 44 and 46 of cap 40 (FIG. 10A) to other lines within main unit 12. In particular, one of openings 44 and 46 of cap 40 illustrated in FIG. 10A is sealed removably to a sewage line extending though main machine 12, through hose 250, to waste container 210 of workhead 200, so that waste material can be pulled from workhead 200 into sewage bucket 30. The other one of openings 44 and 46 of cap 40 illustrated in FIG. 10A is sealed removably to a pneumatic line leading to negative pressure or vacuum source 50, so that main processor 14 can selectively command negative pressure to be applied from source 50 to sewage bucket 30 and waste container 210 of workhead 200 to produce the above-described waste removal.

Figure 11:
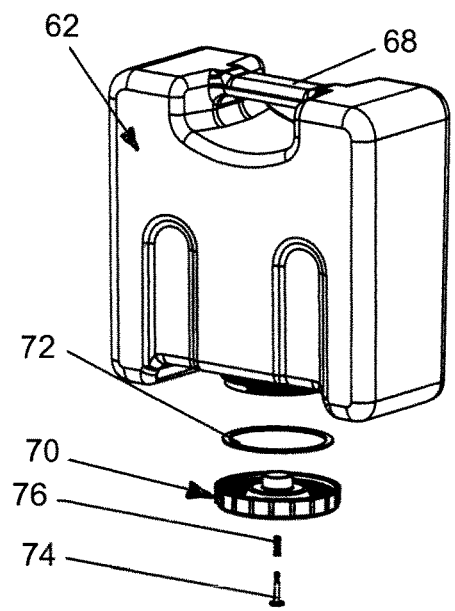
FIG. 11 is a perspective view of one embodiment of a fresh water bucket of the nursing system of the present disclosure.

FIG. 11 illustrates fresh water bucket 62 in more detail. As discussed above, fresh water bucket includes a handle 68 for removing the bucket from main unit 12 and transporting it to a water tap 66 for filling. Fresh water bucket 62 includes a removable cap 70 that sealingly and releaseably threads to the bucket via O-ring 72. Cap 70 includes a check valve 74, which is spring loaded via spring 76. Spring-loaded check valve 74 is biased closed when bucket 62 is being transported outside of main unit 12. When bucket 62 is placed into main unit 12, cap 70 and check valve 74 come to rest on a cup having a centralized pin 88 (illustrated in FIG. 12), which compresses spring 76 and opens check valve 74, allowing fresh water to flow from bucket 62 through a fresh water line extending thorough hose 250 to workhead 200 for flushing and rinsing.

Figure 12:
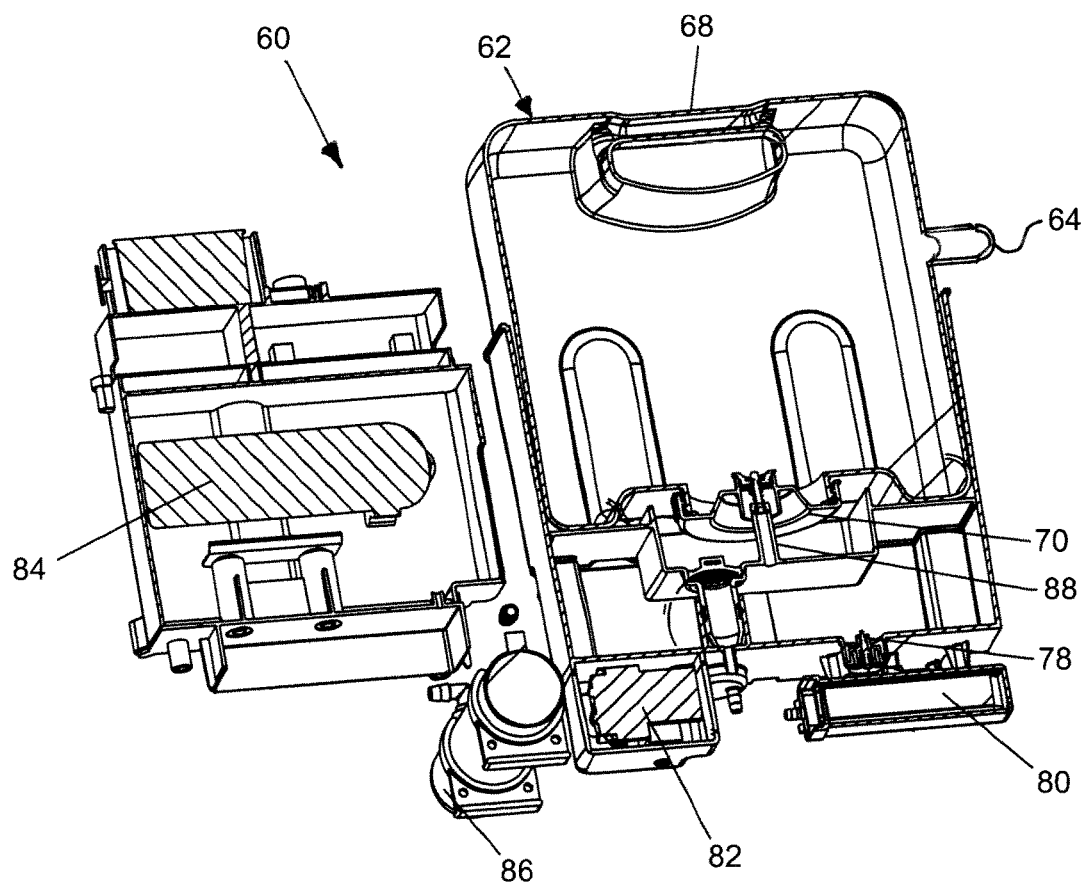
FIG. 12 is a perspective view of one embodiment of a fresh water subassembly of the nursing system of the present disclosure.

FIG. 12 illustrates that fresh water bucket 62 is part of a fresh water subassembly 60. Fresh water subassembly 60 in the illustrated embodiment includes fresh water bucket 62, a three-way valve 78, a heating device 80, such as a positive temperature coefficient ("PTC") heating device, a smaller water pump 82, a larger water pump 84, and an ultraviolet ("UV") disinfector 86. In an embodiment, three-way valve 78, heating device 80, smaller water pump 82, larger water pump 84, and an ultraviolet ("UV") disinfector 86 are all under control of main processor 14 of main unit 12.

FIG. 12 illustrates that fresh water line (tube, pipe or hose) 64, extending to water tap 66, feeds into fresh water bucket 62. Alternatively, FIG. 11 illustrates that fresh water bucket 62 is removed for filling. Otherwise, fresh water subassembly 60 is the same for both FIG. 11 and FIG. 12 versions of fresh water bucket 62. Fresh water subassembly 60 creates an inner heating loop that includes fresh water bucket 62, three-way valve 78, heating device 80, smaller water pump 82, UV disinfector 86, and a temperature sensor (not illustrated) positioned and arranged to output a temperature signal indicative of the temperature of fresh water within fresh water bucket 62.

Main processor 14 can for example receive a flushing or rinsing signal sent by local workhead processor 214 of a workhead 200. If main unit 12 is of the type illustrated in FIG. 12 with fresh water line 64, a water inlet valve placed along line 64 is opened, so that fresh water from tap 66 can enter fresh water bucket 62. A sensor, such as a capacitive, inductive or optical sensor, sends a signal to main processor 14, which detects when fresh water bucket 62 is full and closes the water inlet valve accordingly. If main unit 12 is of the type illustrated in FIG. 11, a user fills fresh water bucket 62 manually. In either case, when bucket 62 is full, main processor 14 causes three-way valve 78 to open a fluid access between bucket 62, heating device 80, smaller water pump 82, and UV disinfector 86. Main processor 14 causes smaller water pump 82 to circulate fresh water multiple times through heating device 80 and UV disinfector 86 for heating and disinfection, before returning to fresh water bucket 62.

After the clean water in the fresh water bucket 62 is heated to a set temperature as measured by a temperature sensor outputting to main processor 14, main processor 14 causes three-way valve 78 to close the heating loop and instead open fresh water access, e.g., via three-way valve 78, to larger water pump 84. Main processor 14 concurrently causes heating device 80 and UV disinfector 86 to be depowered. The circulation via valve 78 and pump 82 can be done before and/or while the waste material removal and cleaning/flushing sequences between main unit 14 and workhead 200 are being performed. Larger water pump 84 is sized to convey, and energized by main processor 14 to convey, the heated and disinfected water from fresh water bucket 62 to waste container 210 of workhead 200 for flushing or rinsing.

Figure 13:
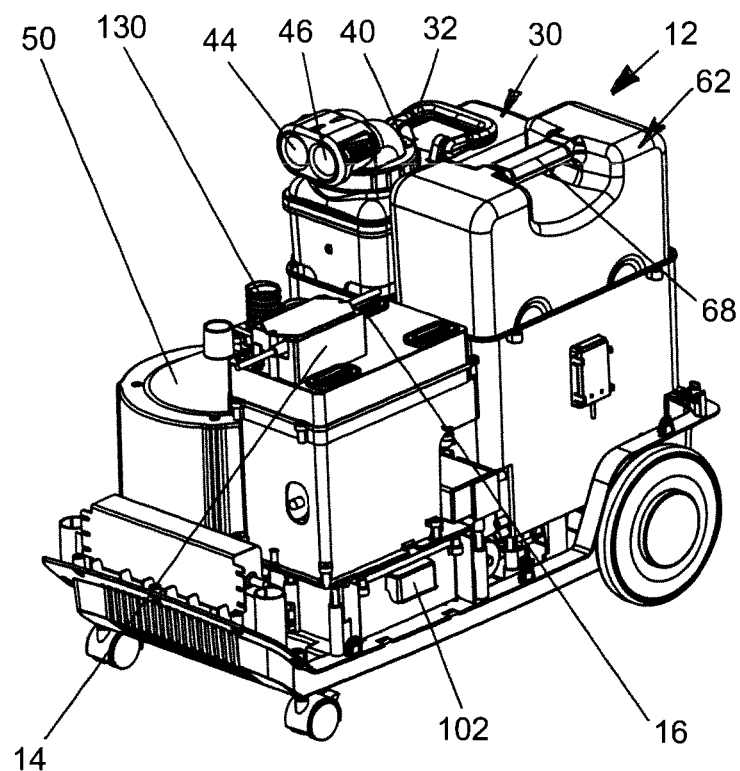
FIG. 13 is a top-front perspective view of one embodiment of a main unit of the nursing system of the present disclosure with housing panels removed.

FIG. 13 illustrates main unit with all of the access panels removed, showing for example, where main unit processor 14 and a main unit communication module 16 (shown in FIG. 16) are located. FIG. 13 also illustrates sewage bucket 30 and fresh water bucket 62 in place for operation. Negative pressure source 50 is also illustrated. Further, the location of deodorization component 102 on main unit 12 is illustrated. Deodorization component 102 is in one embodiment connected with and arranged on the air outlet of the negative pressure source 50. The smell caused within sewage bucket 30 is discharged outwards through the negative pressure source 50 under the evacuation effect of the negative pressure source 50, Deodorization until 102 filters the air exhausted by the negative pressure source 50, tending to prevent odor from being transferred into the hospital room or care area.

Figure 14:
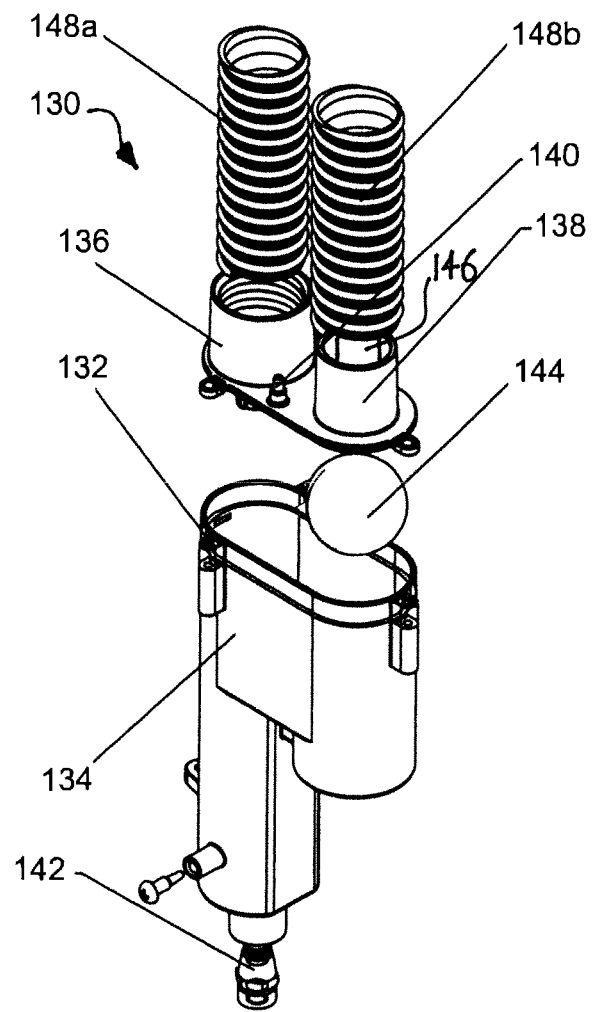
FIG. 14 is a perspective view of one embodiment of a water trap of the nursing system of the present disclosure.

FIG. 13 also illustrates that a water trap 130 is located along the negative pressure air line (tube, pipe or hose) located between sewage bucket 30 and negative pressure source 50. FIG. 14 illustrates water trap 130 in more detail. Water trap 130 prevents the water and water vapor sputtered into sewage bucket 30 from being sucked into negative pressure source 50, potentially damaging the negative pressure source. Water trap 130 includes a pedestal 132 and an impounding cup 134. An intake adapter 136 and an exhaust adapter 138 are provided at the upper end of pedestal 132. Impounding cup 134 is located inline with intake adapter 136 at the lower end of the pedestal 132. A sensor 140 for detecting a liquid level within impounding cup 134 is arranged along the sidewall of impounding cup 134. Sensor 140 can be a capacitive, inductive or optical sensor that provides an output to main processor 14. A drain cock 142 is arranged at the lower end of the impounding cup 134. An impermeable ball 144 provided in pedestal 132 is matched with exhaust adapter 138. A filtering joint 146 is located at the upper end of the exhaust adapter 138.

Intake adapter 136 is connected fluidly with sewage bucket 30 via a water line (tube, pipe or hose) 148a. Exhaust adapter 138 is connected fluidly with negative pressure source 50 via air line (tube, pipe or hose) 148b. Negative pressure applied within water trap 130 via negative pressure source 50 could pull water or water vapor from sewage bucket 30 into impounding cup 134. Any such fluid however falls to the bottom of cup 134 instead of forcing its way around impermeable ball 144, through filtering joint 146, into air line 148b and negative pressure source 50. When the water in impounding cup 134 reaches sensor 140, sensor 140 sends a corresponding output to main processor 14, which in turn tells the user to drain the water from impounding cup 134 by unthreading drain cock 142 from the bottom of the cup, allowing water to fall into an external container. System 10 can provide the alert and corresponding instructions to the user via voice guidance from speaker 26, via an audible alarm from speaker 26, and/or via a message displayed visually on user interface 18. Drain cock 142 is then threaded back into impounding cup 134, allowing system 10 to resume operation.

Centralized, Integrated Version of Nursing System

Figure 15:
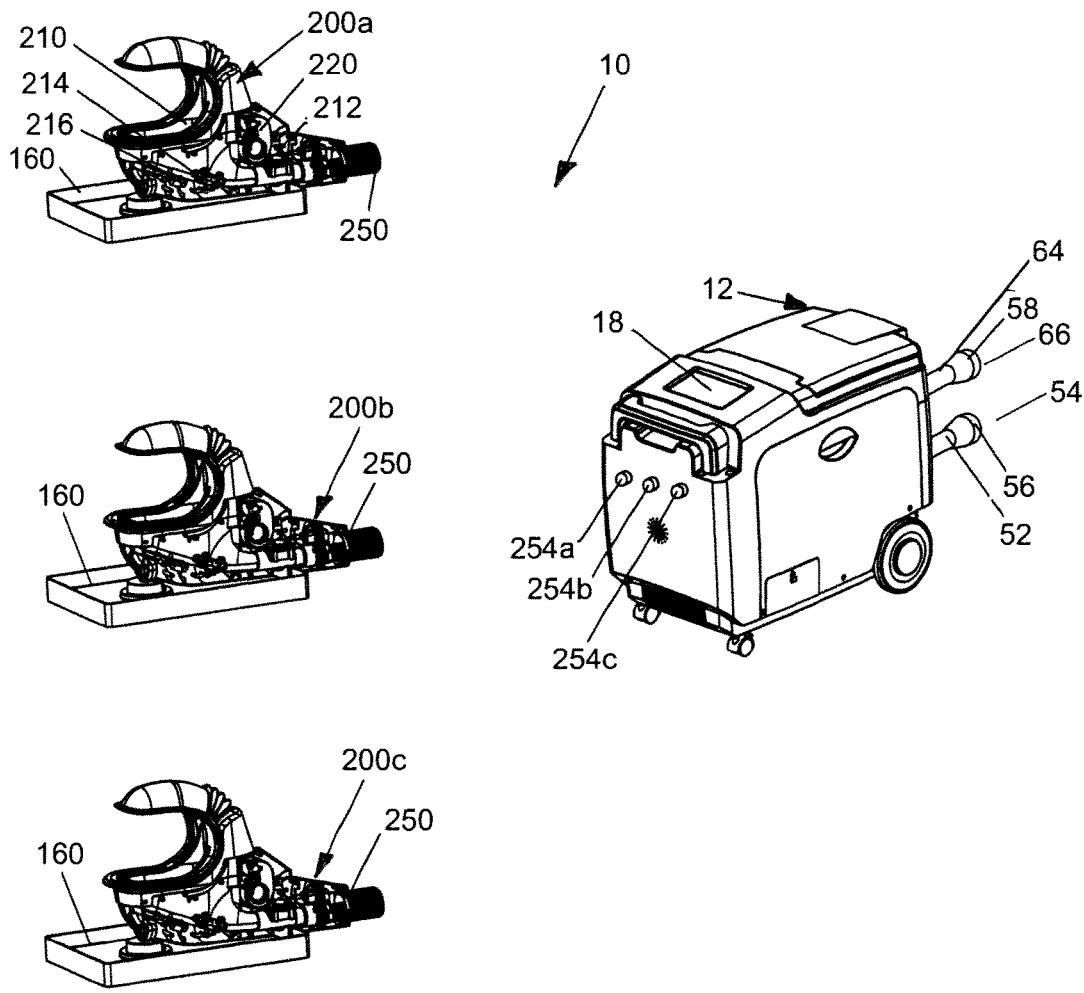
FIG. 15 is a perspective view of one embodiment of a central, integrated version of the nursing system of the present disclosure operable with multiple workheads.
Figure 16:
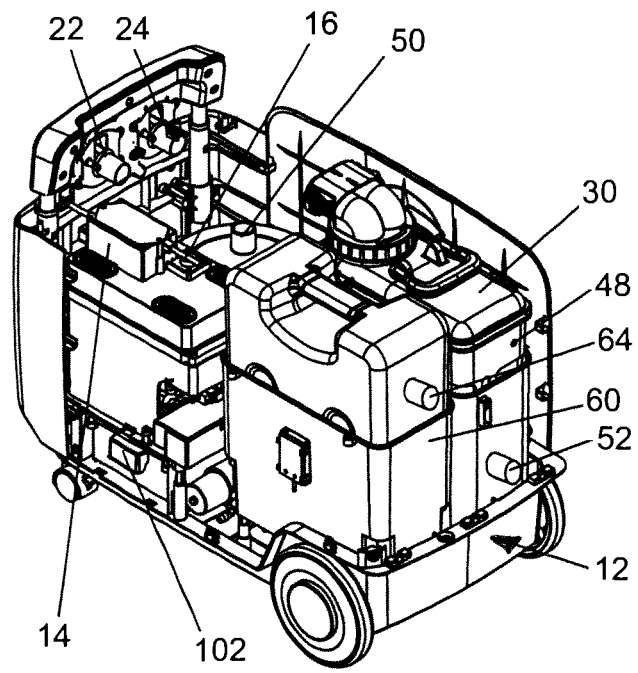
FIG. 16 is a top-rear perspective view of one embodiment of a main unit for the central, integrated version of the nursing system of the present disclosure.

Referring now to FIGS. 15 and 16, one embodiment for a centralized, integrated version of nursing system 10 is illustrated, in which main unit 12 operates a plurality of workheads 200a, 200b, 200c . . . 200n. Main unit 12 here includes the same components as described above for single workhead system 10, such as main processor 14, main communication module 16, user interface 18, sewage bucket 30, negative pressure source 50, fresh water subassembly 60 including fresh water bucket 62, deodorization component 102, and the water trap.

Additionally, main unit 12 in FIGS. 15 and 16 includes a drainage line 52 (tube, pipe or hose), which extends from sewage container 30 (FIG. 16) to a house drain, toilet or sewer 54. An electrical solenoid drain valve 56 (e.g., normally closed) is placed in drain line 52 and in electrical communication with main processor 14. One or more sensor 48 (FIG. 16), such as a capacitive, inductive or optical sensor, is positioned and arranged to look for the waste material level in sewage bucket 30. When the waste material level reaches the sensor, the sensor output changes, which is detected at main processor 14. Main processor 14 then sends a signal to open drain valve 56 to allow waste material to drain (e.g., gravity drain) to house drain, toilet or sewer 54.

The above arrangement avoids shutdown of main machine 12 and workheads 200a to 200c (FIG. 15) due to the waste material being full in either workheads 200a to 200c or sewage bucket 30. System 10 accordingly reduces the need for regular checking and cleaning of sewage bucket 30 by a nurse or caregiver.

Likewise, main unit 12 in FIGS. 15 and 16 includes a fresh water line 64 (tube, pipe or hose) that extends from fresh water bucket 62 to tap water source 66. An electrical solenoid fresh water valve 58 (e.g., normally closed) is placed in fresh water line 64 and in electrical communication with main processor 14. One or more sensor (not illustrated), such as a capacitive, inductive or optical sensor, is positioned and arranged to look for the fresh water level in fresh water bucket 62. When the fresh water level falls to the level sensed by the sensor, the sensor output changes, which is detected at main processor 14. Main processor 14 then sends a signal to open fresh water valve 58 to allow fresh water to feed (e.g., gravity feed) into fresh water bucket 62. A second sensor, such as a capacitive, inductive or optical sensor, can be located to determine when fresh water bucket 62 is full, causing main processor 14 to close fresh water valve 58 to stop filling.

The above arrangement avoids shutdown of main machine 12 and workheads 200a to 200c (FIG. 15) due to the lack of fresh water for any of workheads 200a to 200c. System 10 accordingly reduces the need for regular checking of fresh water bucket 62 by a nurse or caregiver.

It should be appreciated that the addition of drain line 52, drain line valve 56, fresh water line 64 and fresh water valve 58 is not limited to the version of system 10 in which main unit 12 operates with multiple workheads 200 and can alternatively be used even if main machine 12 operates with only a single workhead 200. The primary difference in main machine 12 for the centralized, integrated version of nursing system 10 is the addition of pneumatic manifold 22 (FIG. 16), which selectively distributes waste material suction to different ones of workheads 200a to 200c, and water manifold 24 (FIG. 16), which selectively distributes fresh water to different ones of workheads 200a to 200c for flushing and rinsing.

Pneumatic and water manifolds 22 and 24 as discussed above can include a series of electrically actuated solenoid valves (e.g., normally closed), for example, a different solenoid valve for each workhead 200a to 200c. The valves each control flow through different waste material/pneumatic or water lines extending though different hoses 250, emanating from different main unit connectors 254a to 254c (FIG. 15). Thus in FIG. 15, a first hose 250 extends from first main unit connector 254a to first workhead 200a, a second hose 250 extends from second main unit connector 254b to second workhead 200b, while a third hose 250 extends from third main unit connector 254c to third workhead 200c, and so on to connector 254n and workhead 200n. Each of hoses 250 in one embodiment carries a separate waste material/pneumatic line from pneumatic manifold 22 and a separate water line from water manifold 24. In an alternative embodiment, each of hoses 250 carries a single line (tube, pipe or hose) that is shared by both pneumatic manifold 22 and water manifold 24, which in general require the use of the shared line at different times.

Pneumatic and water manifolds 22 and 24 enable each of workheads 200a to 200c to be operably connected with a single sewage bucket 30 and a single fresh water subassembly 60, respectively, located within main unit 12. Workheads 200a to 200c are each arranged on a separate bed, indicated in FIG. 15 by a separate support tray 160 for each workhead. Each workhead 200a to 200c works independently according to its own stool sensor 222 and a urine sensor 224. Each workhead 200a to 200c, after detecting excrement via stool sensor 222 or urine sensor 224, sends a signal to main unit 12, e.g., via electrical signal communication, wired data, e.g., Ethernet, communication, or wireless, e.g., Wi-Fi, Bluetooth or ZigBee, interface. From there, main processor 14 in an embodiment takes over to control a negative pressure source 50 and fresh water subassembly 60 to operate with the corresponding workhead 200a to 200c according to a predetermined program. In one implementation, main processor 14 takes over completely once receiving the signal from workhead 200, running both negative pressure source 50 waste removal and fresh water subassembly 60 flushing sequences without further input from workhead 200. In an alternative implementation, main processor 14 receives multiple signals from workhead 200, e.g., a first signal to run a negative pressure source 50 waste removal sequence and a second signal to run a fresh water subassembly 60 flushing sequence.

If two workheads 200 require attention at the same time, main processor 14 can remove waste material and then flush the workheads at the same time or stagger the operations, e.g., according to which workhead 200 signaled main unit 12 first. If one of the workheads 200 has to wait for another workhead to be completed, main processor 14 can send a signal to the waiting workhead's remote controller 110 informing the patient that system 10 is currently in use but will be available shortly.

One or more of the negative pressure source 50 waste removal and fresh water subassembly 60 flushing sequences can be different depending upon whether workhead stool sensor 222 or urine sensor 224 is triggered. For example, it may require less negative pneumatic pressure, fresh water pressure and/or fresh water volume to clean urine versus stool from waste container 210 and the patient. System 10 allows different sequences to be optimized differently for different patient and waste sensing conditions.

Workheads

Figure 18:
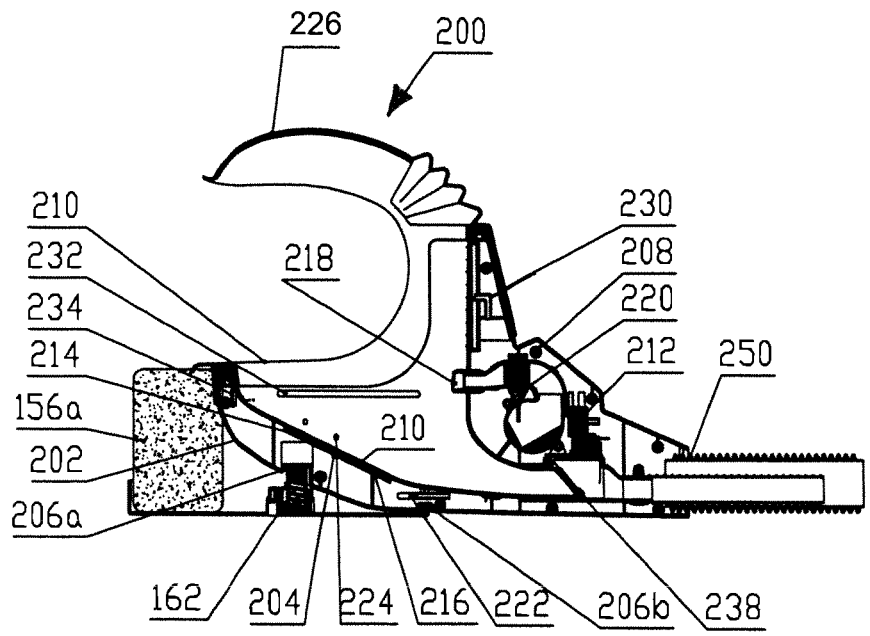
FIG. 18 is a sectioned side elevation view of one embodiment of a workhead of the nursing system of the present disclosure.

FIGS. 15 and 17 to 21 illustrate workheads 200 and related connections in more detail. Each workhead 200 is provided with a waste container 210, a drying device or heating unit 220, a fresh water manifold 212, optionally a local workhead processor 214, and optionally a local workhead communication module 216. Each workhead 200 includes a rubber, e.g., silicone cover 226, which as discussed above covers the patient's private areas, and is held to the patient via garment 170. Silicone cover 226 attaches to the base of workhead 200, which is identified generally as waste container 210. FIG. 18 illustrates that a printed circuit board ("PCB") 204 is located between waste container 210 and an outer wall 202 of workhead 200. PCB 204 provides an electrical base for local workhead processor 214 and local workhead communication module 216. PCB 204 also provides the electrical base to receive the inputs from the various sensors discussed herein for workhead 200 and for powering heating unit 220.

Figure 17:
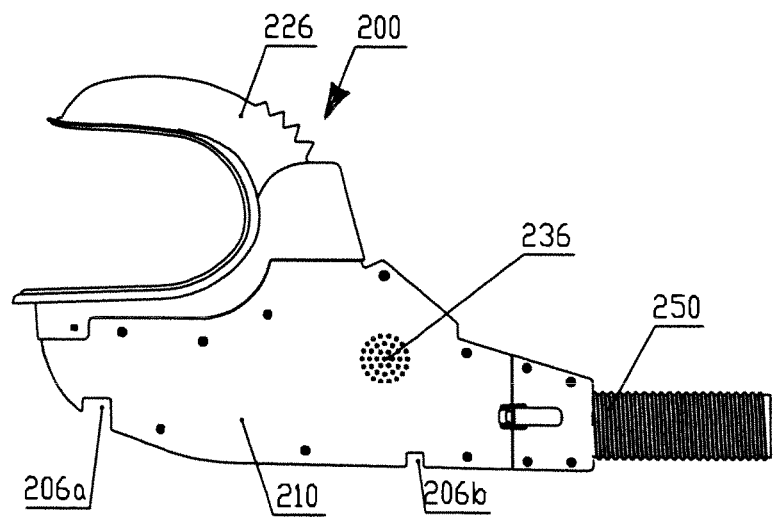
FIG. 17 is a side elevation view of one embodiment of a workhead of the nursing system of the present disclosure.

As discussed above, workhead 220 includes two location slots illustrated in FIGS. 17 and 18 as slots 206a and 206b. Slot 206a of workhead 220 rests upon a spring-loaded, arced pedestal 162 of tray 160, while slot 206b rests upon a cutout 164 provided in the mating end wall of tray 160. The connection of the workhead slots 206a and 206b to tray 160 prevents workhead 200 from sliding back and forth along the long axis of mattress 150. FIG. 18 also illustrates workhead 220 resting on notched pad 156a discussed above in connection with FIG. 2.

Figure 19A:
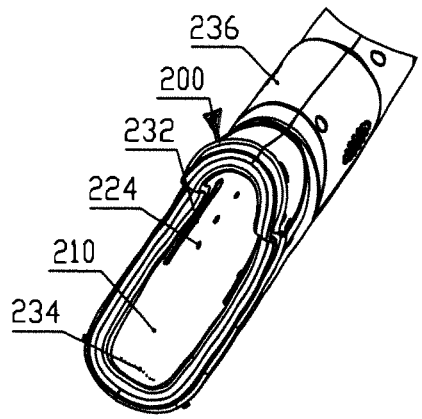
FIGS. 19A and 19B are top-rear perspective views of one embodiment of a workhead of the nursing system of the present disclosure.
Figure 19B:
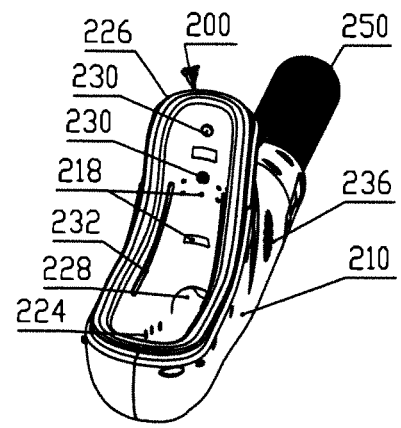

As discussed herein, each workhead 200 includes a fresh water manifold 212 as illustrated in FIG. 18. In an embodiment, workhead processor 214 controls fresh water manifold 212 to selectively carry out a cleaning operation according to a set program. Manifold 212 in an embodiment includes an electrically actuated, e.g., normally closed solenoid valve for each of a plurality of sets of nozzles or sprayers, e.g., a solenoid valve for upper and lower private part nozzles 230 (FIG. 19B), a solenoid valve for side flushing nozzles 232, and a solenoid valve for waste material flushing nozzles 234. Upper and lower private part nozzles 230 are in one embodiment arranged on the wall of the waste container 210 illustrated in FIG. 19B. Side flushing nozzles 232 as illustrated in FIGS. 19A and 19B are in one embodiment arranged along the sides of the waste container 210. Side flushing nozzles 232 in an embodiment can also be translated back and forth along the sides of waste container 210 via a mechanical shifter for optimization. Waste material flushing nozzles 234 are in one embodiment arranged as illustrated in FIG. 19A, so as to be positioned to move stool and urine towards the exit 228 (FIG. 19B) of waste container 210.

Workhead processor 214 can cause any one or more of nozzles 230, 232 or 234 to spray the inner surfaces of waste container 210 and/or the body parts of the patient. The number and sequences of nozzles 230, 232 or 234 used, as well as the water pressure and/or water temperature delivered to the nozzles can be varied according to a computer program, for example, depending upon whether stool or urine has been detected.

FIGS. 18, 19A and 19B illustrate that in one embodiment, stool sensor 222 is placed at the center bottom of waste container 210, while multiple urine sensors are spread out along the bottom of waste container 210. Stool sensor 222 and urine sensor 224 are connected electrically with local workhead processor 214 or alternatively with main processor 14. Stool sensor 222 is in one embodiment a pressure or strain gauge sensor, while urine sensor 224 is in one embodiment a wetness sensor, such as a conductivity sensor. Local workhead processor 214 after receiving a signal or a changed signal from one of sensors 222 or 224 sends a corresponding cleaning start-up signal to main processor 14 of main unit 12 in one embodiment. In another embodiment, the signals from sensors 222 and 224 can be sent to main processor 14, which thereafter initiates the waste material removal and cleaning sequences.

As discussed herein, local workhead processor 214 or main processor 14 can also control the activation of drying device or heating unit 220. Heating unit 220 in an embodiment includes both an air heater and a fan for blowing the heated air. In the illustrated embodiment, the fan of heating unit 220 draws air from air inlet 236. As illustrated in FIG. 18, heating unit 220 is located between waste container 210 and an upper wall 208 of workhead 200. FIGS. 18 and 19B illustrate that drying device or heating unit 220 directs heated air through air ducts 218 onto the private areas of the patient and onto the inner walls of waste container 210. Workhead processor 214 or main processor 14 activates heating unit 220 at the end of a rinse or flush cycle in an embodiment. The amount and temperature of hot air provided can depend for example upon whether stool or urine is sensed and/or how much flushing water is used. In an alternative embodiment, main processor 14 controls heater unit 220 to provide the drying sequence after the removal and cleaning sequences.

The number and sequences of nozzles 230, 232 or 234 used, the water pressure and/or temperature delivered to the nozzles as well as the temperature and volume of hot air can also be varied depending upon the output of a body part identification sensor 240, which is delivered to workhead processor 214 or main processor 14. Body part identification sensor 240 can, for example, be an optical detector or camera, the output of which is analyzed by the receiving processor to identify male versus female, adult versus child, etc., body parts. The result of the processor analysis can then be used to automatically select water temperature, water pressure, air temperature, and/or nozzle selection, for example.

FIG. 18 illustrates that workhead 220 in one embodiment includes a flapper or seal valve 238 to prevent odor from back flowing into workhead. When workhead 200 is not in an active state, seal valve 238 remains closed to isolate waste container 210 of workhead 220 from the sewage bucket 30 of main unit 12. The isolation helps to prevent any smell from sewage bucket 30 from being transferred through waste container 210 to the patient and surrounding area.

Figure 21:
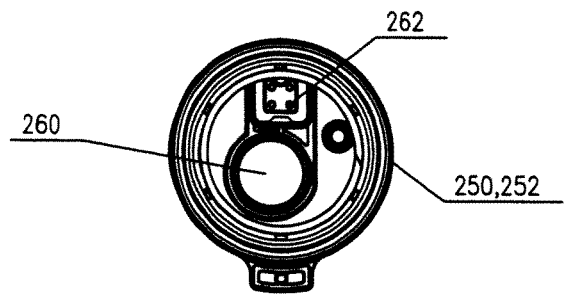
FIG. 21 is a front view of one embodiment of a hose connector of the nursing system of the present disclosure.
Figure 20:
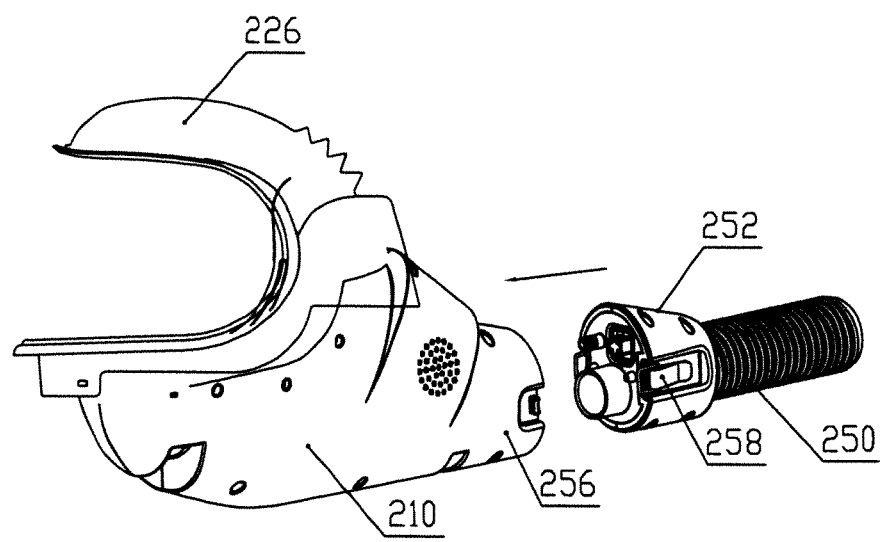
FIG. 20 is a top-rear perspective view of one embodiment of a workhead of the nursing system of the present disclosure having the connection hose removed.

FIGS. 9, 20 and 21 illustrate hose connector 252, which is simply pushed sealingly and removably onto main unit connector 254 and workhead connector 256 in one embodiment. FIG. 20 illustrates that hose connector 252 can be so aligned and releaseably connected via removable buckles 258. FIG. 21 illustrates that hose 250 and hose connector 252 can carry a waste material/pneumatic/water line (hose, tube, pipe) 260 and electrical leads 262. The user can align buckles 258 on hose connector 252 with the buckle catches on main unit connector 254 and workhead connector 256 to in turn automatically align waste material/pneumatic/water line (hose, tube, pipe) 260 and electrical leads 262 of hose 250 with like structure located in main unit connector 254 and workhead connector 256 for sealed and/or proper operational engagement.

Remote Control

Referring now to FIGS. 22 to 26, embodiments of remote controller 110 and its capabilities within system 10 are illustrated. Each of the input functions described herein can be performed alternatively or additionally on a keypad (e.g., touch screen or membrane switch) provided with user interface 18 on main machine 12. It should also be appreciated that if workhead processor 214 and communication module 216 are provided, remote controller 110 can operate with communication modules 16, 216 and processors 14, 214 of both main unit 12 and workhead 200. If workhead processor 214 and communication module 216 are not provided, remote controller 110 operates instead with communication module 16 and processor 14 of main unit 12.

Figure 22:
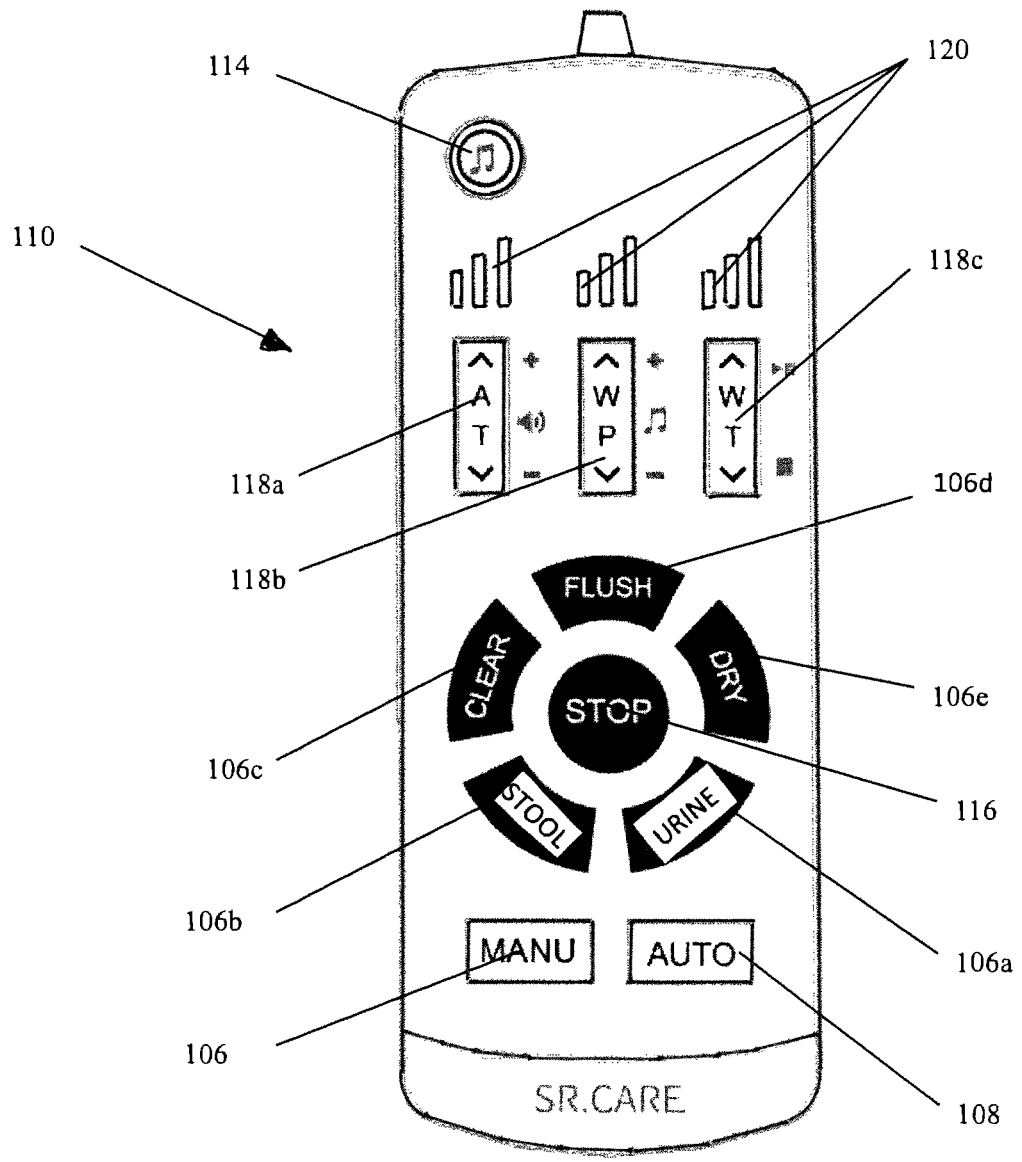
FIG. 22 is a front view of one embodiment of a remote controller for the nursing system of the present disclosure.

FIG. 22 illustrates an embodiment to remote controller 110. Remote controller 110 includes a manual button 106, which shifts system 10 from an automatic mode (e.g., default) to a manual mode. Auto button 108 switches system 10 from a manual mode back to automatic mode. When in manual mode, pressing the #1 button 106a runs a manually initiated urination clean, rinse and dry sequence. When in manual mode, pressing the #2 button 106b runs a manually initiated stool clean, rinse and dry sequence. When in manual mode, pressing clean button 106c runs a manually initiated patient private parts cleaning sequence. When in manual mode, pressing flush button 106d runs a manually initiated flush workhead sequence. When in manual mode, pressing dry button 106e runs a manually initiated patient private parts drying sequence.

Remote controller 110 also includes a music button 114. When the patient or user presses music button 114, system 10 shifts from a care mode to a music mode. The functions of toggle buttons 118a to 118c change when in music mode, allowing the patient to play their personal music player (e.g., select songs, adjust volume, start/stop), such as a smartphone, iPod or MP3 player. Stop button 116 stops any current, ongoing operation.

Toggle button 118a in the care mode allows selection of high, medium and low levels for air temperature. Toggle button 118b in the care mode allows selection of high, medium and low levels for water pressure. Toggle button 118c in the care mode allows selection of high, medium and low levels for water temperature. Bar indicators 120 are displays showing the user the current setting for a particular parameter, e.g., high, medium, or low for air temperature, water pressure, and water temperature.

Figure 23:
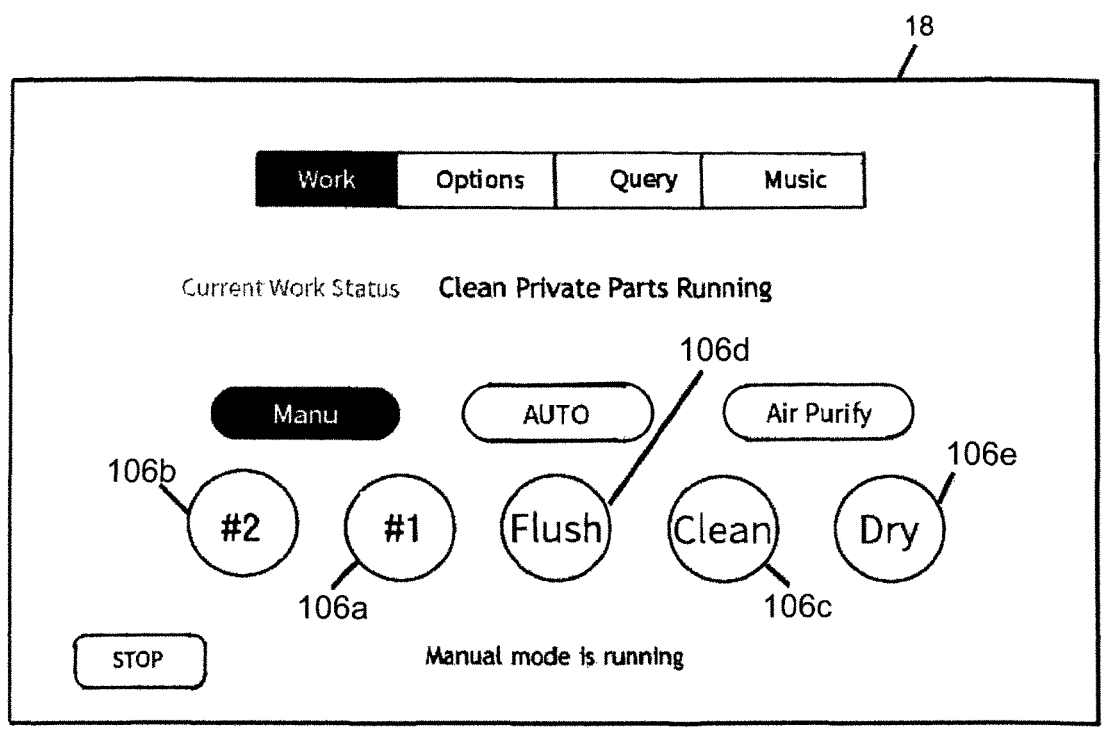
FIG. 23 is a user interface screenshot of one embodiment of a work page for the nursing system of the present disclosure.

FIG. 23 is a screenshot of user interface 18 for main machine 12 illustrating one embodiment of a "Work" page for system 10. Here, the screen of user interface 18 displays current work status, e.g., currently cleaning private parts. Screen 18 shows that the current mode is manual mode. In manual mode, stool sequence, urine sequence, flush sequence, clean sequence, and dry sequence can be selected. In automatic mode, those processes are performed automatically. In clean air ("CA") sequence, clean air is forced through deodorization component 102 to fumigate system 10. If user interface 18 is provided with a touch screen overlay operable with main processor 14, any of stool sequence, urine sequence, flush sequence, clean sequence, and dry sequence displays also act as buttons 106a to 106e, which in manual mode can be selected to run the sequence as described above for remote controller 110.

Figure 24:
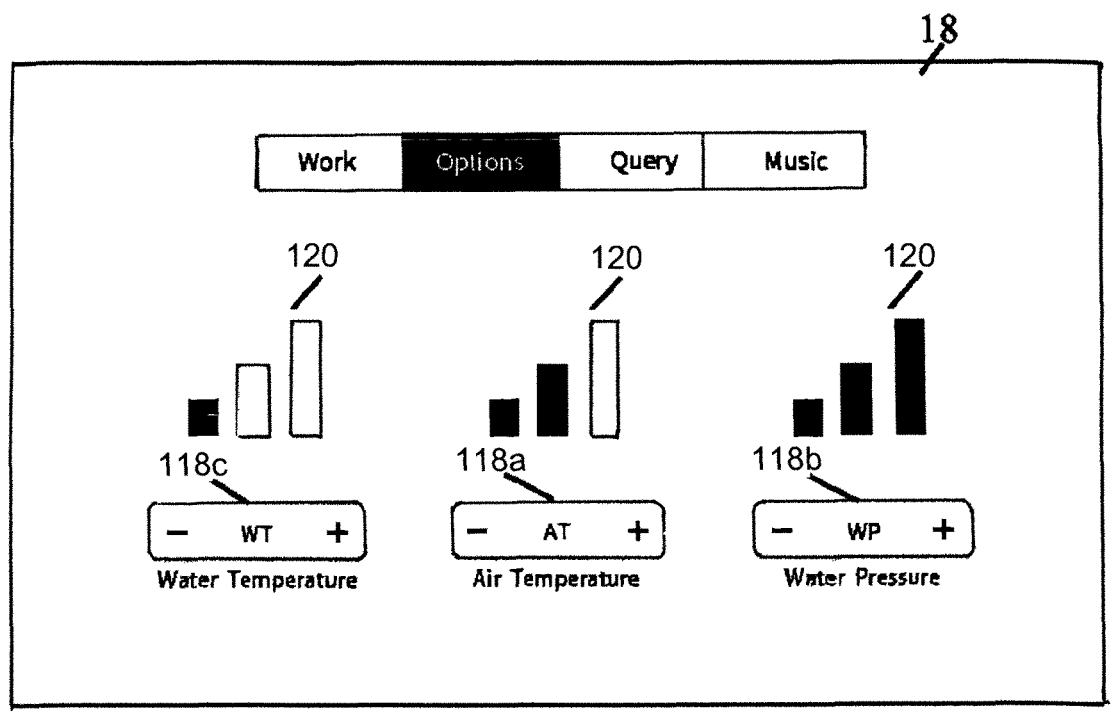
FIG. 24 is a user interface screenshot of one embodiment of a settings page for the nursing system of the present disclosure.

FIG. 24 is a screenshot of user interface 18 for main machine 12 illustrating one embodiment of an "Options" page for system 10. Here, screen 18 displays bar indicators 120 showing the current settings, e.g., low, medium, or high for water temperature, air temperature, and water pressure. Toggle buttons 118a to 118c are provided (for screen 18 having a touch screen) for adjusting air temperature, water pressure, and water temperature, respectively.

Figure 25:
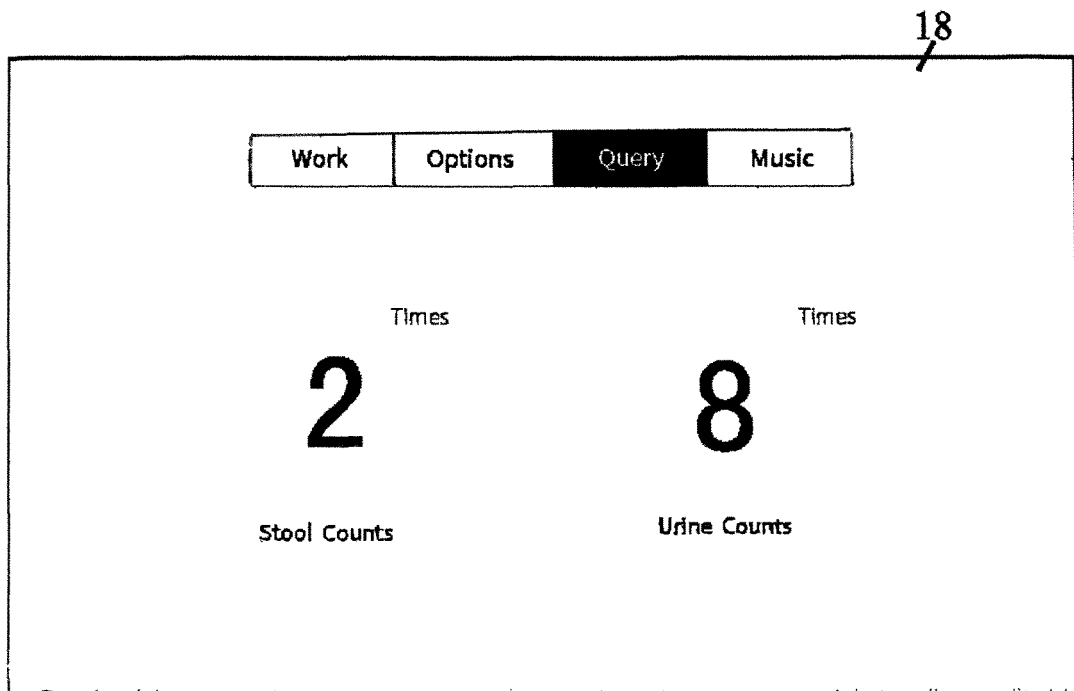
FIG. 25 is a user interface screenshot of one embodiment of an inquiry page for the nursing system of the present disclosure.
Figure 26:
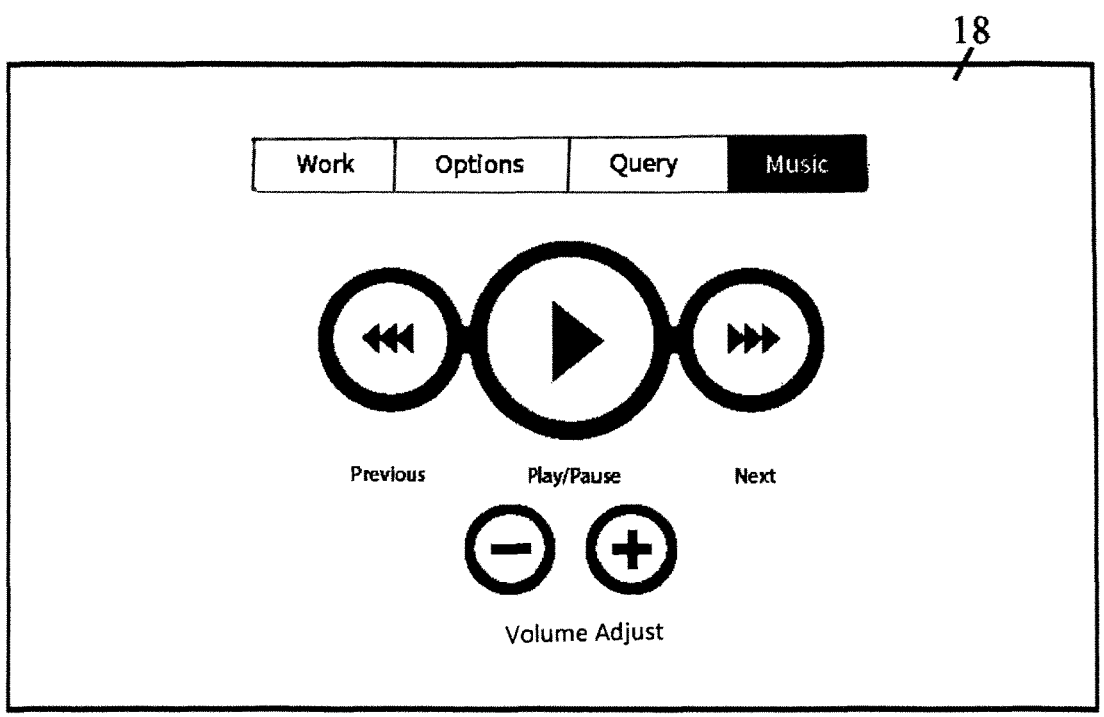
FIG. 26 is a user interface screenshot of one embodiment of a music page for the nursing system of the present disclosure.

FIG. 25 is a screenshot of user interface 18 for main machine 12 illustrating one embodiment of an "Inquiry" page for system 10. Here, screen 18 displays counts, e.g., over the last twenty-four hours, of how many stool and urine sequences have been run. Screen 18 could display similar counts for any one or more of flush, clean, and dry sequences. FIG. 26 is a screenshot of user interface 18 for main machine 12 illustrating one embodiment of a "Music" page for system 10. Here, screen 18 operating with a touch screen displays buttons for selecting or adjusting previous song, next song, play or pause current song, volume up and volume down for current song.

Any one or more of the screenshots of FIGS. 23 to 25 can be placed in a patient folder displayed on a home screen of user interface 18. The home screen for the central, integrated version of system 10 can then display multiple folders for multiple patients being serviced via workheads 200a, 200b, 200c . . . 200n. The user can thereby select the folder for the desired patient to then call forth the corresponding patient-specific screenshots of FIGS. 23 to 25.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention is claimed as follows:

1. An automated nursing system for handling waste material from a patient comprising:
a mattress including an opening;
a workhead for accepting the waste material, the opening of the mattress sized to accept the workhead, the workhead including a sensor for sensing the waste material, a workhead processor for receiving an output from the waste material sensor, and a workhead communication module;
a main unit in water flow and pneumatic pressure communication with the workhead; and
a main processor carried by the main unit, the main unit including a main unit communication module, the workhead processor and the main processor in communication via the workhead communication module and the main unit communication module, the main processor programmed to at least partially (i) cause negative pneumatic pressure to be applied to the workhead to remove the waste material from the workhead upon sensing of the waste material by the waste material sensor, and (ii) cause water to be delivered to the workhead to rinse the patient.

2. The automated nursing system of claim 1, which includes a hose connecting the workhead to the main unit, the hose protecting the water and pneumatic pressure communication between the workhead and the main unit.

3. The automated nursing system of claim 1, wherein the workhead includes a base residing at least mostly within the opening within the mattress, and a cover extending from the base and above the mattress for covering a private area of the patient.

4. The automated nursing system of claim 1, wherein the workhead communication module and the main unit communication module are configured to communicate in a wired manner.

5. The automated nursing system of claim 1, wherein the workhead communication module and the main unit communication module are configured to communicate wirelessly.

6. The automated nursing system of claim 1, which includes a remote controller that interfaces with the main processor.

7. The automated nursing system of claim 1, wherein the waste material sensor includes a urine sensor and a stool sensor, the sensors producing a urine sensor output and a stool sensor output, respectively, used so that the main processor of the main unit can initiate (i) and (ii).

8. The automated nursing system of claim 7, wherein the urine sensor or stool sensor output is delivered to the workhead processor, the workhead processor in data communication with the main unit so that the main processor of the main unit can initiate (i) and (ii).

9. The automated nursing system of claim 7, wherein the delivery of at least one of (i) or (ii) is different depending upon whether the urine sensor output or the stool sensor output is produced.

10. The automated nursing system of claim 1, wherein the workhead includes at least one of a stool flushing nozzle, an upper private patient area flushing nozzle, a lower private patient area flushing nozzle, or a side flushing nozzle.

11. The automated nursing system of claim 10, wherein the workhead includes a manifold for selectively delivering water to at least one of the stool flushing nozzle, upper private patient area flushing nozzle, lower private patient area flushing nozzle, or the side flushing nozzle according to a predetermined sequence.

12. The automated nursing system of claim 1, wherein the workhead includes a hot air outlet positioned and arranged to dry the patient.

13. The automated nursing system of claim 1, wherein the workhead includes a body type identification sensor producing an output used by the main processor or the workhead processor.

14. The automated nursing system of claim 13, wherein the body type identification output is used to control at least one of a level of the negative pneumatic pressure, water pressure, water volume or air temperature.

15. The automated nursing system of claim 1, wherein the workhead includes an air heater and a hot air fan.

16. The automated nursing system of claim 15, wherein the main processor or the workhead processor controls the air heater and the hot air fan to provide hot air to dry the patient.

17. The automated nursing system of claim 1, wherein the workhead defines at least one location slot for securing the workhead to a tray for receiving the workhead, the tray located within the opening of the mattress.

18. The automated nursing system of claim 1, wherein the opening of the mattress receives a pad having a shaped notch for receiving the workhead.

19. The automated nursing system of claim 1, wherein the main unit includes a sewage bucket, the waste material removed from the workhead into the sewage bucket.

20. The automated nursing system of claim 19, which includes a negative pressure source in pneumatic pressure communication with the sewage bucket, the negative pressure source positioned and arranged to pull the waste material from the workhead into the sewage bucket.

21. The automated nursing system of claim 20, wherein the negative pressure source is controlled by the main processor to perform (i).

22. The automated nursing system of claim 20, which includes a water trap located between the sewage bucket and the negative pressure source, the water trap preventing water or water vapor in the sewage bucket from reaching the negative pressure source.

23. The automated nursing system of claim 22, which includes a sensor positioned and arranged with respect to the water trap so as to have an output that can indicate when the water trap needs to be emptied.

24. The automated nursing system of claim 23, wherein the main processor upon receiving the output from the water trap sensor indicating that the water trap needs to be emptied provides a corresponding user message in at least one form selected from: a user readout, an audible alarm or a voice guidance output.

25. The automated nursing system of claim 19, wherein the sewage bucket is configured to be removed from the main unit to empty waste material from the sewage bucket.

26. The automated nursing system of claim 25, which includes a sensor positioned and arranged with respect to the sewage bucket so as to have an output that can indicate when the sewage bucket needs to be emptied.

27. The automated nursing system of claim 26, wherein the main processor upon receiving the output from the sewage bucket sensor indicating that the sewage bucket needs to be emptied provides a corresponding user message in at least one form selected from: a user readout, an audible alarm or a voice guidance output.

28. The automated nursing system of claim 19, wherein the sewage bucket is in fluid communication with a drain line, the drain line for removing waste material from the sewage bucket to a house drain, toilet or sewer.

29. The automated nursing system of claim 28, which includes a valve in the drain line, the drain valve selectively enabling waste material to be removed from the waste bucket.

30. The automated nursing system of claim 29, which includes a sensor positioned and arranged with respect to the sewage bucket so as to have an output that can be used to know when to open the drain valve.

31. The automated nursing system of claim 28, wherein the waste material is gravity fed from the sewage bucket through the drain line.

32. The automated nursing system of claim 1, wherein the main unit includes a fresh water bucket, the water delivered to the workhead from the fresh water bucket.

33. The automated nursing system of claim 32, which includes a water pump in water flow communication with the fresh water bucket, the water pump positioned and arranged to pump water from the fresh water bucket to the workhead.

34. The automated nursing system claim 33, wherein the water pump is controlled by the main processor to perform (ii).

35. The automated nursing system of claim 32, wherein the fresh water bucket includes a spring-loaded valve for allowing water to be delivered from the bucket to the workhead.

36. The automated nursing system of claim 32, wherein the fresh water bucket is in fluid communication with a fresh water line, the fresh water line for delivering fresh water from a source to the fresh water bucket.

37. The automated nursing system of claim 36, which includes a valve in the fresh water line, the fresh water valve selectively enabling fresh water to be delivered to the fresh water bucket.

38. The automated nursing system of claim 37, which includes a sensor positioned and arranged with respect to the fresh water bucket so as to have an output that can be used to know when to open the fresh water valve.

39. The automated nursing system of claim 32, which includes a valve in fluid communication with the fresh water bucket, the valve selectively enabling fresh water from the fresh water bucket to be circulated through at least one of a heater or an ultraviolet ("UV") disinfector.

40. The automated nursing system of claim 39, which includes a temperature sensor positioned and arranged to have an output that can be used to enable fresh water to be circulated until the fresh water reaches a desired temperature.

41. The automated nursing system of claim 40, wherein the desired temperature is reached before (ii) can be performed.

42. The automated nursing system of claim 40, wherein the circulation valve is switched so that (ii) can be performed when the desired temperature has been reached.

43. The automated nursing system of claim 39, wherein fresh water is circulated before and/or while performing (i).

44. The automated nursing system of claim 1, which includes a garment for holding the workhead against the patient.

45. The automated nursing system of claim 1, which is configured to perform (i) and (ii) in an automatic mode or a manual mode, the manual mode enabling user selection of at least one of a stool sequence, a urine sequence, a flush sequence, a clean sequence, or a dry sequence.

46. The automated nursing system of claim 45, wherein at least one of the automatic mode or the manual mode is selected via a remote controller.

47. The automated nursing system of claim 1, wherein at least one operating parameter of the system is user-selectable, the at least one operating parameter including water temperature, water pressure or air temperature.

48. The automated nursing system of claim 1, wherein the workhead is a first workhead, and which includes at least one second workhead in water flow and pneumatic pressure communication with the main unit.

49. The automated nursing system of claim 48, which includes a water flow manifold that allows water to be selectively delivered to the first workhead or to one of the at least one second workheads to perform (ii).

50. The automated nursing system of claim 49, wherein the water flow manifold includes a plurality of solenoid valves controlled by the main processor.

51. The automated nursing system of claim 48, which includes a negative pressure manifold that allows negative pressure to be selectively applied to the first workhead or to one of the at least one second workheads to perform (i).

52. The automated nursing system of claim 51, wherein the negative pressure manifold includes a plurality of solenoid valves controlled by the main processor.

53. An automated nursing system for handling waste material from a patient comprising:
   a mattress including an opening;
   a workhead for accepting the waste material, the opening of the mattress sized to accept the workhead, the workhead including a urine sensor, a stool sensor and a workhead processor, the sensors producing a urine sensor output and a stool sensor output, respectively, the outputs delivered to the workhead processor;
   a main unit in water flow and pneumatic pressure communication with the workhead; and
   a main processor carried by the main unit, the main processor programmed, in response to the urine sensor output or the stool sensor output, to at least partially (i) cause negative pneumatic pressure to be applied to the workhead to remove the waste material from the workhead, and (ii) cause water to be delivered to the workhead to rinse the patient.

54. The automated nursing system of claim 53, wherein the application or delivery of at least one of (i) or (ii) is different depending upon whether the urine sensor output or the stool sensor output is produced.

55. An automated nursing system for handling waste material from a patient comprising:
a mattress including an opening;
a workhead for accepting the waste material, the opening of the mattress sized to accept the workhead;
a main unit in water flow and pneumatic pressure communication with the workhead, the main unit including a sewage bucket, a negative pressure source and a water trap located between the sewage bucket and the negative pressure source, the negative pressure source positioned and arranged to pull the waste material from the workhead into the sewage bucket, and the water trap configured to prevent at least one of water or water vapor in the sewage bucket from reaching the negative pressure source; and
a main processor carried by the main unit, the main processor programmed to at least partially (i) cause negative pneumatic pressure from the negative pressure source to be applied to the workhead to remove the waste material from the workhead, and (ii) cause water to be delivered to the workhead to rinse the patient.

56. The automated nursing system of claim 55, wherein the negative pressure source is controlled by the main processor to perform (i).

57. The automated nursing system of claim 55, which includes a sensor positioned and arranged with respect to the water trap so as to have an output that can indicate when the water trap needs to be emptied.

58. The automated nursing system of claim 57, wherein the main processor upon receiving the output from the water trap sensor indicating that the water trap needs to be emptied provides a corresponding user message in at least one form selected from: a user readout, an audible alarm or a voice guidance output.

59. The automated nursing system of claim 55, wherein the negative pressure source includes a negative pneumatic pressure source.

60. An automated nursing system for handling waste material from a patient comprising:
a mattress including an opening;
a workhead for accepting the waste material, the opening of the mattress sized to accept the workhead;
a main unit in water flow and pneumatic pressure communication with the workhead, the main unit including a fresh water bucket for delivering fresh water to the workhead, the fresh water bucket in fluid communication with a fresh water line, the fresh water line for delivering fresh water from a source to the fresh water bucket, and a fresh water valve in the fresh water line, the fresh water valve selectively enabling fresh water to be delivered to the fresh water bucket; and
a main processor carried by the main unit, the main processor programmed to at least partially (i) cause negative pneumatic pressure to be applied to the workhead to remove the waste material from the workhead, and (ii) cause water to be delivered from the fresh water bucket to the workhead to rinse the patient.

61. The automated nursing system of claim 60, which includes a water pump in water flow communication with the fresh water bucket, the water pump positioned and arranged to pump water from the fresh water bucket to the workhead.

62. The automated nursing system claim 60, wherein the water pump is controlled by the main processor to perform (ii).

63. The automated nursing system of claim 60, wherein the fresh water bucket includes a spring-loaded valve for allowing water to be delivered from the bucket to the workhead.

64. The automated nursing system of claim 60, which includes a sensor positioned and arranged with respect to the fresh water bucket so as to have an output that can be used to know when to open the fresh water valve.

* * * * *